(12) United States Patent
Rhinehart et al.

(10) Patent No.: US 10,328,208 B2
(45) Date of Patent: Jun. 25, 2019

(54) BLOW-MOLDED SYRINGE FOR USE WITH AN INJECTOR

(71) Applicant: BAYER HEALTHCARE LLC, Indianola, PA (US)

(72) Inventors: Edward J. Rhinehart, Monroeville, PA (US); Kevin P. Cowan, Allison Park, PA (US); Mark Trocki, Cheswick, PA (US); Barry L. Tucker, Verona, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 184 days.

(21) Appl. No.: 15/032,425

(22) PCT Filed: Oct. 31, 2014

(86) PCT No.: PCT/US2014/063477
§ 371 (c)(1),
(2) Date: Apr. 27, 2016

(87) PCT Pub. No.: WO2015/066506
PCT Pub. Date: May 7, 2015

(65) Prior Publication Data
US 2016/0271330 A1 Sep. 22, 2016

Related U.S. Application Data

(60) Provisional application No. 61/898,592, filed on Nov. 1, 2013.

(51) Int. Cl.
*A61M 5/178* (2006.01)
*A61M 5/315* (2006.01)
(Continued)

(52) U.S. Cl.
CPC ........ *A61M 5/31513* (2013.01); *A61M 5/178* (2013.01); *B29B 11/14* (2013.01);
(Continued)

(58) Field of Classification Search
CPC .............. A61M 5/31513; A61M 5/178; A61M 2207/00; A61M 2207/10; B29B 11/14;
(Continued)

(56) References Cited

U.S. PATENT DOCUMENTS 3,256,892 A 6/1966 Esposito, Jr.
3,376,999 A 4/1968 Hart et al.
(Continued)

FOREIGN PATENT DOCUMENTS

WO 2012139551 A2 10/2012

OTHER PUBLICATIONS

"May 13, 2016—PCT_IPRP_with_Written_Opinion_(dated May 12, 2015) for PCT Appln. No. PCT/US2014/063477".
(Continued)

*Primary Examiner* — Michael C Miggins
(74) *Attorney, Agent, or Firm* — Joseph L. Kent; David Schramm; James R. Stevenson

(57) ABSTRACT

A syringe for use in pressurized injection of a fluid is provided herein. The syringe includes a syringe barrel comprising a polymeric material having undergone expansion by stretch blow molding and by compression molding of an inner diameter of the barrel with a core member. In certain configurations of the syringe barrel, the stretch blow molding is provided through a nozzle of the syringe. Similarly, according to a further embodiment, a syringe for use in pressurized injection of a fluid is provided. The syringe includes a syringe barrel comprising a polymeric material
(Continued)

having undergone expansion by stretch blow molding and by shrinking an inner diameter of the syringe barrel about a core member.

16 Claims, 27 Drawing Sheets

(51) Int. Cl.
B29B 11/14 (2006.01)
B29C 49/18 (2006.01)
B29C 49/12 (2006.01)
B29L 31/00 (2006.01)

(52) U.S. Cl.
CPC ............. *B29C 49/12* (2013.01); *B29C 49/18* (2013.01); *A61M 2207/00* (2013.01); *A61M 2207/10* (2013.01); *B29B 2911/1402* (2013.01); *B29B 2911/1404* (2013.01); *B29B 2911/14026* (2013.01); *B29B 2911/14033* (2013.01); *B29B 2911/1442* (2013.01); *B29B 2911/14328* (2015.05); *B29B 2911/14332* (2015.05); *B29B 2911/14335* (2015.05); *B29B 2911/14486* (2013.01); *B29B 2911/14533* (2013.01); *B29B 2911/14573* (2013.01); *B29C 2049/1228* (2013.01); *B29C 2049/1238* (2013.01); *B29C 2791/006* (2013.01); *B29C 2791/007* (2013.01); *B29L 2031/753* (2013.01); *B29L 2031/7544* (2013.01)

(58) Field of Classification Search
CPC ... B29B 2911/1402; B29B 2911/14026; B29B 2911/14033; B29B 2911/1404; B29B 2911/1442; B29B 2911/14486; B29B 2911/14533; B29B 2911/14328; B29B 2911/14335; B29B 2911/14332; B29B 2911/14573; B29C 2049/1228; B29C 2049/1238; B29C 2791/006; B29C 2791/007; B29C 49/18; B29C 49/12; B29L 2031/753; B29L 2031/7544
See application file for complete search history.

(56) References Cited

U.S. PATENT DOCUMENTS

| 3,855,380 | A | 12/1974 | Niemi et al. |
| 3,923,943 | A | 12/1975 | Iriko et al. |
| 4,039,641 | A | 8/1977 | Collins |
| 4,244,409 | A | 1/1981 | Wilson et al. |
| 4,342,184 | A | 8/1982 | Van Eck et al. |
| 4,411,656 | A | 10/1983 | Cornett, III |
| 4,681,606 | A | 7/1987 | Swan, Jr. et al. |
| 4,790,822 | A | 12/1988 | Haining |
| 5,047,017 | A | 9/1991 | Koska |
| 5,061,252 | A | 10/1991 | Dragosits |
| 5,122,327 | A | 6/1992 | Spina et al. |
| 5,242,422 | A | 9/1993 | Schneberger et al. |
| 5,330,425 | A | 7/1994 | Utterberg |
| 5,383,858 | A | 1/1995 | Reilly et al. |
| 5,873,861 | A | 2/1999 | Hitchins et al. |
| 5,900,205 | A | 5/1999 | Sadr et al. |
| 6,017,330 | A | 1/2000 | Hitchins et al. |
| 6,041,775 | A | 3/2000 | Century |
| 6,224,577 | B1 | 5/2001 | Dedola et al. |
| 6,394,983 | B1 | 5/2002 | Mayoral et al. |
| 6,652,489 | B2 | 11/2003 | Trocki et al. |
| 6,665,489 | B2 | 12/2003 | Collart |
| 6,673,303 | B2 | 1/2004 | White et al. |
| 6,719,733 | B1 | 4/2004 | Heffernan et al. |
| 6,984,222 | B1 | 1/2006 | Hitchins et al. |
| 7,175,609 | B1 | 2/2007 | Gray |
| 7,740,792 | B2 | 6/2010 | Haury et al. |
| 8,728,601 | B2 | 5/2014 | Hutts et al. |
| 2002/0048642 | A1 | 4/2002 | Beck |
| 2002/0055719 | A1 | 5/2002 | Lo |
| 2003/0121927 | A1 | 7/2003 | Rice et al. |
| 2004/0262818 | A1 | 12/2004 | Takeuchi |
| 2005/0148720 | A1 | 7/2005 | Li et al. |
| 2005/0161866 | A1 | 7/2005 | Batlaw et al. |
| 2006/0029720 | A1 | 2/2006 | Panos et al. |
| 2008/0157444 | A1 | 7/2008 | Melsheimer |
| 2008/0200916 | A1 | 8/2008 | Murphy et al. |
| 2010/0241085 | A1 | 9/2010 | Haury et al. |
| 2012/0031870 | A1 | 2/2012 | Porter et al. |
| 2013/0281940 | A1 | 10/2013 | Gelblum et al. |

OTHER PUBLICATIONS

International Search Report and the Written Opinion dated Mar. 23, 2015 from corresponding PCT Application No. PCT/US2014/063477.

Admer, Mitsui Chemicals America, Inc. of Rye Brook, New York, (www.mitsuichemicals.com/cha.htm), Retrieved from the Internet Sep. 11, 2007.

Lamonte, R.R. and D. McNally, Cyclic Olefin Copolymers, Advanced Materials & Processes, (Mar. 2001), 4 pages.

Whitmore, E.M., "Standards & Practices of Plastics Molders—Guidelines for Molders and Their Customers, Molders Division," Sponsored by the Society of the Plastics Industry, Inc. (1993).

Zeonor 1410R, Zeon Chemicals LP of Louisville, Kentucky, Material Safety Data Sheet, Oct. 18, 2002.

"Supplementary Partial European Search Report in EP Application No. EP14857772", dated Sep. 26, 2017.

"Supplementary Partial European Search Report from EP Application No. EP14857772", dated Sep. 26, 2017.

BLOW-MOLDED SYRINGE FOR USE WITH AN INJECTOR

CROSS REFERENCE TO RELATED APPLICATIONS

This application is a 371 national phase application of PCT International Application No. PCT/US2014/063477, filed Oct. 31, 2014, and designating the United States of America, which claims priority to U.S. Provisional Application No. 61/898,592, entitled "Blow-Molded Syringe For Use With An Injector" and filed on Nov. 1, 2013. The disclosures of which are incorporated herein by reference in their entirety.

BACKGROUND

Field of the Technology

The present disclosure relates generally to disposable syringes for use with injectors and to methods of manufacture thereof, and, more particularly, to syringes and methods of manufacture using blow molding processes.

Description of Related Art

In many medical procedures, such as drug delivery, it is desirable to inject a fluid into a patient. Likewise, numerous types of contrast media used in imaging procedures (often referred to simply as contrast) are injected into a patient for many diagnostic and therapeutic procedures, for example, gene therapy, cell and biological agent delivery, and delivery of therapeutic agents generally. For example, contrast media are used in diagnostic procedures such as X-ray procedures (including, for example, angiography, venography, urography), computed tomography (CT) scanning, magnetic resonance imaging (MRI), and ultrasonic imaging. Contrast media are also used during therapeutic procedures, including, for example, angioplasty and other interventional radiological procedures.

A number of injector-actuated syringes and powered injectors for use in medical procedures such as angiography, computed tomography (CT), ultrasound, and NMR/MRI have been developed. A front-loading syringe and injector system is, for example, disclosed in U.S. Pat. No. 5,383,858, assigned to the assignee of the present application, the disclosure of which is incorporated herein by reference. Other front-loading syringes and injector systems are, for example, disclosed in U.S. Pat. No. 6,652,489, the disclosure of which is incorporated herein by reference.

Historically, it has been difficult to manufacture syringes with desirable transparent optical properties that exhibit sufficient strength for use with front-loading, pressure jacketless injectors. Indeed, depending upon the application, syringe pressures in the range of 300 psi to 1200 psi are commonly experienced in injection procedures using powered injectors. Typically, to achieve suitable strength, the syringe walls must be thickened during manufacture, which increases costs and, depending upon the material, can degrade optical properties. However, in current injection molding practices for manufacturing syringes, there is a limit to the wall thickness that can be achieved. This limit can result in syringes designed with a lower safety factor than desirable. Moreover, as wall thickness is increased, production costs also increase. For example, increases in wall thickness are associated with longer injection times, longer packing times, higher pressures, longer cooling times, and increased resin costs.

In view of these challenges, it has been proposed to produce syringes from a blow molding process to produce syringes having thinner walls and increased tensile strength. Blow molding is a method of forming hollow articles from thermoplastic polymeric materials. The blow molding process involves forming a heated article within a mold cavity using a pressurized gas (typically, compressed air) to expand the heated thermoplastic to conform to the walls of the mold cavity. The three most common methods of blow molding are extrusion blow (EB) molding, injection blow (IB) molding, and injection-stretch blow (ISB) molding. In EB molding, tubes or parisons are extruded into alternating open mold halves and then blown and cooled prior to removal from the mold. In IB molding, a "preform" component is first injection molded. The preform is then blown to the product's final shape. Injection blow molding can provide dimensional precision in certain critical areas. In the ISB molding process, a preform is, once again, first injection molded. During subsequent blow molding, the preform/parison is mechanically extended or stretched at an optimal temperature, while radially blown to shape within the mold. ISB molding provides a biaxial stretch to enhance material properties. Syringes and methods of manufacture thereof using ISB blow molding processes are disclosed in U.S. Pat. No. 7,740,792 which issued on Jun. 22, 2010, and which is hereby incorporated by reference herein in its entirety.

However, one potential drawback of blow molding for syringes for medical applications is that it may be difficult to control the inner diameter of the syringe since only the outer wall of the syringe barrel contacts the mold. Therefore, it is often difficult to manufacture a syringe by blow molding having an inner diameter within a desired tight tolerance. In addition, the syringes produced by blow molding processes may have different structural and sealing characteristics compared with standard injection molded syringes, as are known in the art. The various embodiments of the syringes and methods of manufacture described herein are designed to address such issues.

BRIEF SUMMARY

According to one aspect, a syringe for use in pressurized injection of a fluid is provided herein. The syringe includes a syringe barrel comprising a polymeric material having undergone expansion by stretch blow molding and by compression molding of an inner diameter of the barrel with a core member. In certain configurations of the syringe barrel, the stretch blow molding is provided through a nozzle of the syringe. Similarly, in another preferred and non-limiting embodiment, a syringe for use in pressurized injection of a fluid includes a syringe barrel comprising a polymeric material having undergone expansion by stretch blow molding and by shrinking the inner diameter of the syringe barrel about a core member.

In accordance with a further aspect, a syringe for use in pressurized injection of fluid includes a flexible syringe barrel and a plunger configured to be advanced through the barrel to eject fluid therefrom. An outer diameter of the plunger is larger than the inner diameter of the syringe barrel.

In accordance with a further aspect, a system for compacting syringes formed from a polymeric material is provided. The system includes a heating chamber for heating the syringes above a glass transition temperature of the polymeric material and a compactor for compressing the syringes to form a disposable structure.

Another aspect of the disclosure provides a preform for stretch blow molding a syringe. The preform comprises a body having a distal end, a proximal end, and a circumferential wall therebetween and comprising a polymeric material suitable for stretch blow molding to form a syringe body; and a first opening at the distal end of the body for inserting a stretch member for stretching the preform during a stretch blow molding process, wherein an inner walls of the stretch blow molded preform have a substantially uniform inner diameter for slidably receiving a plunger.

The preform may comprise a cap for sealably enclosing the first opening, the cap having a substantially conical shape and comprising a nozzle and a luer tip. The cap may further comprise at least one bayonet lock member around an outer circumference of the cap for releasably locking engagement with at least one notch or slot on a pressure jacket configured for attachment to a medical injector. In various embodiments, a second opening at a proximal end of the body for slidably receiving the plunger may be formed after the stretch blow molding process.

In some embodiments, the body may be formed having the stretch member in an interior of the body, wherein the diameter of the stretch member is larger than the diameter of the distal opening and wherein the stretch member has a substantially conical end for forming the distal end of the preform into a substantially conical shape during the stretch blow molding process. The stretch member may be formed from a material selected from the group consisting of a second polymeric material having a glass transition temperature higher than the polymeric material of the preform, a composite material, and a metal material. The stretch member may further comprise a lumen and a plurality of ports for injecting a gas into the interior of the body during the stretch blow molding process. The stretch member may be removed through a second opening at a proximal end of the body formed after the stretch blow molding process. The second opening may be formed for slidably receiving a plunger. The substantially conical shape of the distal end of the preform may be configured to fit into a pressure jacket comprising a substantially conical distal end.

In some embodiments, the preform may comprise a second opening at the proximal end for receiving the stretch member, wherein the stretch member seals the first opening during a stretch blow molding process through the second opening. The proximal end of the preform may comprise at least one retaining member for reversible engagement with a complementary locking member on a syringe port of a medical injector. The inner diameter of the inner surface of the walls may be molded by insertion of a core member through the second opening. The core member may be an expandable core comprising a flexible sheet coiled around an inner member, wherein the flexible sheet may transition between a first compressed state and a second expanded state. The core member may be an expandable core comprising an expandable balloon for receiving a fluid. The inner surface of the walls may be molded around the core member by application of vacuum or pressure and heat to shrink the walls of the preform against the core. The core member may be tapered from a proximal end to a distal end.

Another aspect of the disclosure provides a stretch blow molded syringe. The stretch blow molded syringe comprises a body having a distal end, a proximal end, and a circumferential wall therebetween; a nozzle having a luer tip; at least one retaining member for reversible engagement with a complementary locking member on a syringe port of a medical injector; and a proximal opening for slidably receiving a plunger comprising at least one radially extending sealing member, wherein an outer diameter of the plunger is greater than an inner diameter of the circumferential wall of the body, such that the at least one radially extending sealing member form a sealing engagement with the circumferential wall and deflect the circumferential wall outward at the engagement site. The circumferential wall may be deflected outward to contact an inner wall of a pressure jacket. The circumferential wall may substantially deflect inward to an original inner diameter after the plunger has passed.

Another aspect of the disclosure provides a method for stretch blow molding a syringe for a medical injector, the method comprising stretch blow molding a preform; and inserting a core member into the preform during a stretch blow molding to mold an inner diameter of the preform to a substantially uniform inner diameter, wherein the core member has a uniform outer diameter substantially equal to the desired substantially uniform inner diameter of the syringe. The method may further comprise applying heat and one of pressure or vacuum to the preform while inserting the core member to compress an inner wall of the preform to an outer wall of the core member. The core member may be an expandable core member and the method may further comprise expanding the expandable core member to compress an inner wall of the preform to an outer wall of the expandable core member.

These and other features and characteristics of syringes, syringe connection interfaces, and systems having syringes and/or syringe connection interfaces, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

BRIEF DESCRIPTION OF THE DRAWINGS

Some of the advantages and features of the preferred embodiments of the disclosure have been summarized hereinabove. These embodiments, along with other potential embodiments of the device, will become apparent to those skilled in the art when referencing the following drawings in conjunction with the detailed descriptions as they relate to the figures.

DETAILED DESCRIPTION

Figure 1A:
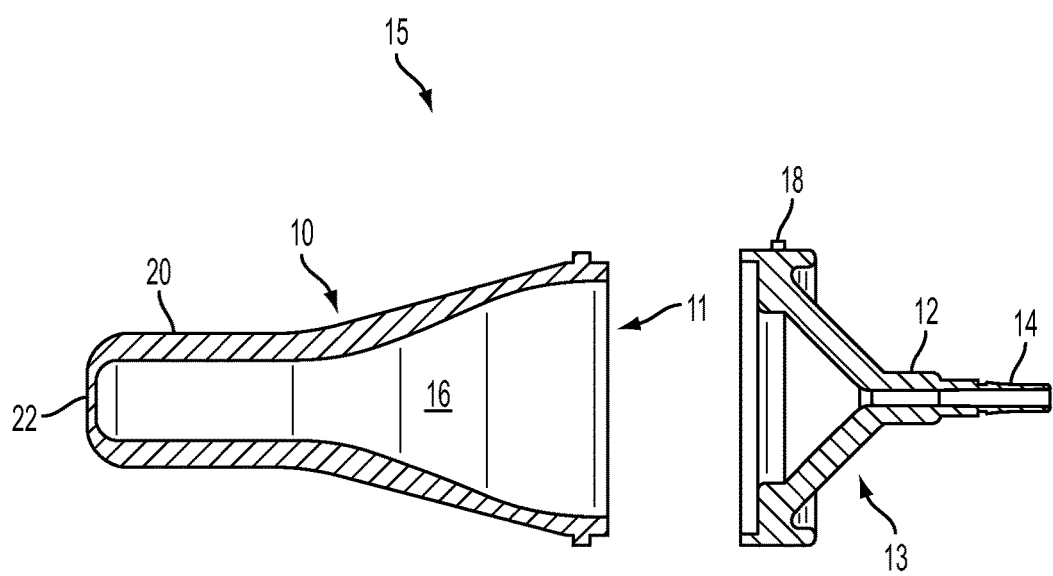
FIG. 1A is a schematic drawing of an injection molded preform of a syringe, according to the principles of one embodiment.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to the preform for the blow molded syringe, the term "proximal" refers to the portion of the preform which receives the stretch rod and into which air is directed. The term "distal" refers to the portion of the preform farthest away from the blow molding device. Similarly, when used to refer to a finished syringe, the term "proximal" refers to the portion of a syringe that engages an injector or is held by a user. The term "distal" refers to the portion of the syringe farthest away from a body of an injector or the hand of a user. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

The present disclosure provides a syringe for use in a pressurized injection of a fluid, for example using a medical injector. The syringe includes a syringe barrel including a polymeric material having undergone expansion via blow molding. An inner diameter of the syringe barrel can, for example, be sufficiently constant (over at least a portion of the axial length of the syringe) that a plunger slidably positioned within the syringe barrel and in generally sealing contact with an inner wall of the syringe barrel can be used within the syringe barrel to generate a pressure to inject a fluid contained within the syringe barrel. The syringes of the present invention can be used in both low pressure and high pressure application. For example, the uniformity of the inner diameter of the syringe barrels of the syringes of the present invention is suitable to generate a pressure of at least 1 psi within the syringe barrel or of, for example, at least 100 psi within the syringe barrel. In several embodiments, the diameters of the inner walls of the syringe barrels of the present invention are suitably constant to generate a pressure of at least 200 psi, at least 300 psi, or even at least 500 psi within the syringe barrel. The inner diameter of the syringe wall can, for example, vary no more than 0.01 in. The inner diameter of the syringe can also vary by no more than 0.007 in. or even no more than 0.004 in. The syringe barrels can, for example, withstand relatively high pressures. For example, the syringe barrel can withstand pressures of at least 1 psi, at least 100 psi, at least 150 psi, at least 200 psi, at least 300 psi, at least 500 psi or even at least 1200 psi. The walls of the syringe barrel can be relatively thin. For example, the wall of the syringe barrel can be less than 0.07 inches in thickness or even less than 0.05 inches in thickness. Examples of blow molding procedures and syringe structures that may be useful in various embodiments of the present disclosure are described in U.S. Pat. Nos. 7,740,792 and 8,747,726; and U.S. application Ser. Nos. 12/794,990, 12/794,920, 13/453,335, 13/834,624, and 13/881,072; the disclosures of each of which are incorporated herein in their entirety.

The polymeric material can, for example, undergo biaxial orientation via injection stretch blow molding. In several embodiments, the polymeric material of the syringe includes, for example, at least one of polyethylene terephthalate (PET), cyclic olefin polymer, polypropylene, polystyrene, polyvinylidene chloride, polyethylene naphthalate (PEN) or nylon. The polymeric material can be a co-injected material of one or more of the above identified polymers and/or other polymers. Examples of co-injected materials include, but are not limited to, PET/PEN or PET/nylon. The syringe can include a first layer of a first polymeric material and at least a second layer of a second polymeric material, different from the first polymeric material. At least one of the first polymeric material can, for example, include polyethylene terephthalate, cyclic olefin polymer, polypropylene, polystyrene, polyvinylidene chloride, polyethylene naphthalate or nylon. The first and/or the second polymeric material can, for example, include a single polymer or blends of two or more polymers. As used herein, the term "polymer" includes homopolymers which are synthesized from a single monomer and copolymers which are synthesized from two or more different monomers. The polymeric materials of the first layer and the second layer can, for example, differ in one or more respects such as composition, molecular weight, crystallinity, barrier properties etc.

The syringe can, for example, include one or more portions, sections or components that are molded to certain predefined acceptable tolerances for a predefined use. Such molded portions, sections or components are sometimes referred to herein as "precision molded" portions, sections or components. For example, the syringe can include one or more attachment mechanisms positioned, for example, to the rear of the syringe barrel. Likewise, one or more attachment mechanism and/or other precision molded portions can be formed on or in the vicinity of the forward end of the syringe, in the vicinity of the syringe outlet.

In another aspect, the present invention provides a method of forming a syringe including the steps of: injection molding at least one polymeric material to form a preform; placing the preform into a blow mold die; and expanding at least a portion of the preform within the die to form a barrel of the syringe. Those components, elements, portions or sections of the preform to be blow molded/expanded (for example, the barrel portion of the syringe) are typically heated (above the glass transition ($T_g$) of the polymeric material(s)) prior to placing the preform within the blow mold die. During the preheating process, precision molded components, portions or sections of the preform can be protected from heating (that is, maintained at a lower temperature) to, for example, maintain molded dimensions within acceptable tolerances. Those portions or sections of the preform to be expanded within the blow mold die can also be heated during the blow molding process. The syringes can be formed for use at low pressure or to withstand relatively high pressures as described above. The at least one polymeric material can, for example, be polyethylene terephthalate, cyclic olefin polymer, polypropylene, polystyrene, polyvinylidene chloride, polyethylene naphthalate or nylon. The method can further include a heat setting process.

Injection molding the preform can, for example, include forming one or more portions molded to dimension of predefined acceptable tolerance such as an attachment mechanism (positioned, for example, adjacent a proximal or rearward end of the syringe), which is adapted to connect the syringe to, for example, a powered injector. The attachment mechanism can, for example, include at least one flange. The tolerances of precision molded portions such as injector attachment mechanisms are maintained during blow molding. For example, the attachment mechanism or other precision molded portion is not altered or substantially altered (for example, such that an attachment mechanism does not suitably retain the syringe upon an injector) during the expansion of the preform. Injection molding the preform can also include forming a connector or other precision molded portion adjacent a distal end of the preform. The connector or other precision molded portion is not altered or substantially altered during expansion of the preform.

Expanding at least a portion of the preform can include forcing of a gas within the preform and axial extension of an extension rod within the preform. Injection molding the preform can also include forming a syringe outlet section at a distal end of the preform, wherein the preform includes a passage between a barrel section thereof and the syringe outlet section. The extension rod can, for example, form at least a partial seal with the passage during expansion of the preform. In several embodiments, injection molding the preform can also include forming a connector or attachment mechanism (for example, a Luer connector) during injection molding of the preform as described above, which is positioned adjacent the distal end of the preform. Once again, the connector is not altered or substantially altered during expansion of the preform.

With reference to the figures, various embodiments of a preform 10 and blow-molded syringe 100 are presented herein. The preform 10 is formed into a predetermined shape by injection molding. The preform 10 may be formed from a thermoplastic material, such as polyethylene terephthalate (PET), cyclic olefin polymer, polyethylene, polypropylene, polystyrene, polyvinylidene chloride, polyethylene naphthalate (PEN), nylon, or any combination thereof. These thermoplastic materials have a relatively low glass transition temperature, meaning that little energy is required to heat the preform 10 prior to molding. For example, the glass transition temperature of PET is about 160° F. to 180° F. The preform 10 may have any of a wide variety of configurations. For example, the preform 10 may include at least one opening for receiving a stretch rod and for applying blowing air into an interior of the preform 10. If the preform 10 includes more than one opening, then the stretch rod must cover the extra opening during blow molding so that air does not escape. The preform 10 may also include various structural elements, such as flanges, luer connectors, bayonet locks, nozzles, and the like. It is noted that structural elements near the end of the preform 10 that receives the stretch rod do not expand or change shape during the stretch blow molding process. Structural portions of the opposite end of the preform 10 are more likely to deform during stretching or blow molding. The injection molded preform 10 is stretched and blow molded to form a finished syringe.

Generally, the finished syringe includes a proximal opening, a substantially cylindrical syringe barrel, and a distal end having a luer connector forming a nozzle. A plunger and piston rod may be inserted through the proximal opening. Reversibly advancing the piston rod and plunger through the syringe barrel draws in and expels fluid through the distal nozzle.

FIGS. 1A-1D illustrate a preform 10 and a blow-molded syringe 100 in accordance with the principles of one embodiment of the present disclosure. As described above, the preform 10 is molded by an injection molding process. The injection molding process is well suited for formation of areas of a syringe 100 in which dimensions are critical and in which tight tolerances must be maintained. In one embodiment, blow molding precursor 15 includes preform 10 and cap 13. A nozzle 12 and luer lock 14 are positioned on one end of the cap 13, which may also include at least one bayonet lock member 18 around an outer circumference of the cap 13. The preform 10 includes a first opening 11 for accessing an interior 16 of the preform 10. The stretch rod and blown air are introduced into the interior 16 of the preform 10 through the first opening 11. In another embodiments, the at least one bayonet lock member 18 may be provided on the end of the preform 10 near the first opening 11. As described herein, these structures on the end of the preform 10, near the first opening 11, remain essentially unchanged following stretching and blow molding. Further, the cap is not involved in the stretch blow molding process and is attached to the expanded preform 10 after the process. Thus, the cap 13, including luer lock 14, nozzle 12, and bayonet lock 18, may be molded to a high degree of specificity. The preform 10 further includes a cylindrical wall 20 extending between an enclosed end 22 of the preform 10 and the end of the preform near the first opening 11.

Figure 1B:
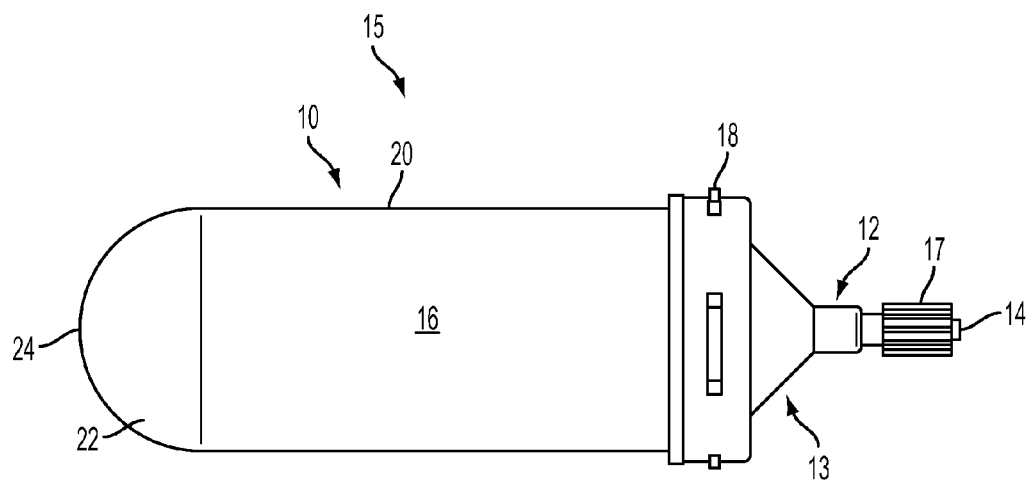
FIG. 1B is a schematic drawing of the preform of FIG. 1A, after expansion by stretch blow molding.

The preform 10 is configured to undergo stretching and blow molding to result in the expanded preform 10 depicted in FIG. 1B. In the stretch blow molding process, a stretch rod is inserted into the interior 16 of the preform 10 through the first opening 11. The stretch rod is extended, pressing against the enclosed end 22 of the preform 10, while compressed air or other gas is blown into the interior 16 of the preform 10. The preform 10 expands to fill a mold cavity (not shown) positioned around the outside of the preform 10. The cylindrical wall 20 of the expanded preform 10 is formed from a thermoplastic material that is biaxially oriented when stretched, resulting in a thin wall structure having excellent tensile strength. The stretch rod remains in the interior 16 of the expanded preform 10 until cooling is complete. Once the molded preform 10 cools, the stretch rod is removed. The molded preform 10 may then be used to produce a finished syringe 100 (FIG. 1C).

As described above, the nozzle 12 and luer lock 14 on the cap 13 are essentially unchanged by the stretch blow molding process and may have dimensional stability substantially corresponding to the completed syringe. The distal end of the preform 10 including first opening 11 may also remain unchanged during the stretch blow molding process so that it may form a sealing engagement, for example by glue or other adhesive, spin welding or other welding process, or by a threaded engagement with cap 13. To further preserve these structures, steps may be taken during stretching and blow molding to cool this portion of the preform 10 to below the glass transition temperature of the thermoplastic resin to prevent material deformation. Alternatively or in addition to cooling means, a heat shield may be used to block these structural elements from heat applied to the remainder of the preform 10 during molding. Additionally, heat may be applied selectively to different areas of the preform 10 above the distal end. For example, differential heating elements may be employed to heat different portions of the preform 10 to different temperatures.

As shown in FIG. 1B, the stretch blow molding process forms a dome-shaped end cap 24 on the enclosed proximal end 22 of the expanded preform 10 (shown with cap 13 attached). The dome-shaped end cap 24 may be cut off the preform 10 to produce the finished syringe 100. The finished syringe 100 includes an open proximal end 122. The dome-shaped cap 24 may cut at a location sufficient to form a substantially square bottom creating a substantially uniform cylindrical syringe barrel 116. However, with use of a pressure jacket 200 some variation in tolerance may be acceptable since total volume of the fluid in the syringe is determined by the volume between the plunger 128 and the distal end 126 of the syringe 100.

Figure 1C:
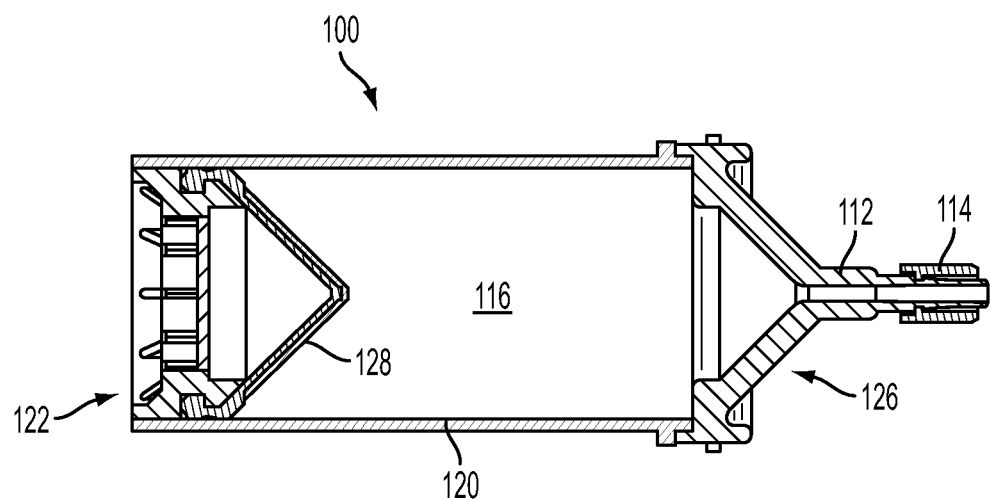
FIG. 1C is a schematic drawing of a syringe formed from the preform of FIG. 1A including a plunger.

With reference to FIG. 1C, a finished syringe 100 formed by stretch blow molding is depicted. The syringe 100 has a proximal opening 122, thin walled cylindrical barrel 120, and cap 113 including bayonet lock members 118, a tapered nozzle 112 and luer tip 114 at a distal end 126 of the barrel 120. The nozzle 112 is enclosed within a luer lock 114. A plunger 128 is inserted into the proximal opening 122 of the syringe 100. The syringe 100 is adapted for insertion into an injector, such as a power injector for injection of a contrast agent or saline solution to a patient through a catheter or needle. In one non-limiting embodiment, the syringe 100 may be inserted into a pressure jacket 200. The pressure jacket 200 is connected to the injector (not shown). A schematic drawing of a pressure jacket 200 and syringe 100 is depicted in FIG. 1D.

Figure 1D:
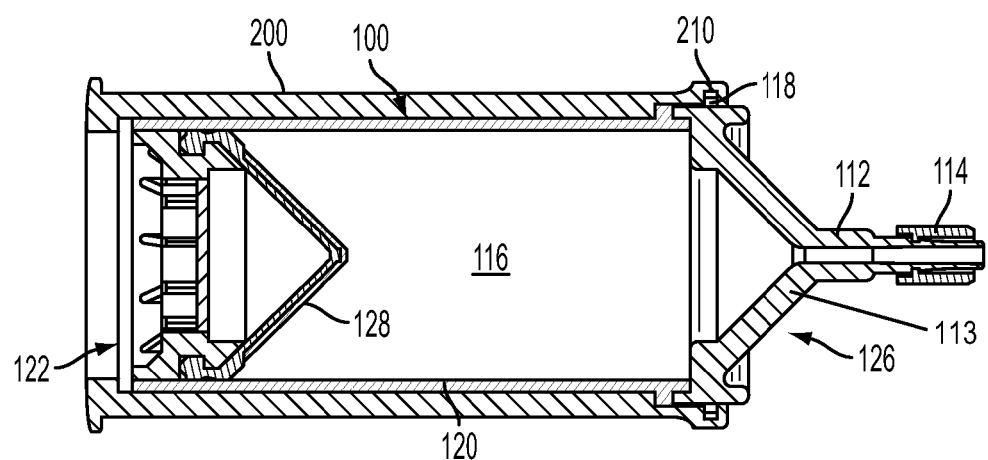
FIG. 1D is a schematic drawing of a pressure jacket for use with the syringe of FIG. 1C.

The pressure jacket 200 depicted in FIG. 1D includes notches 210 or indentations corresponding to bayonet lock members 118 on the distal end 126 of the syringe 100. Insertion of the bayonet lock members 118 within the notches 210 of the pressure jacket 200 effectively positions and locks the syringe 100 within the pressure jacket 200. Since the position of the syringe 100 is determined based on the connection between the distal end 126 of the syringe 100 and the notches 210, the length of the barrel 120 is not critical. However, to maintain the uniformity of a manufacturing process, it may be desirable that the length of the barrel 120 is maintained within a predefined tolerance range. As such, it is not critical where the dome-shaped cap 24 of the expanded preform 10 is cut. It is only necessary that the barrel 120 is of sufficient length to fit within pressure jacket 200 and to permit full motion of the plunger 128 for the syringe 100.

In some embodiments, the pressure jacket 200 provides additional support and strength for the syringe 100. As has been described herein, the syringe 100 formed by blow molding has thinner walls compared with conventional syringes produced wholly by injection molding. Thus, the additional support and strength provided by the pressure jacket 200 may be beneficial. In certain embodiments, the pressure jacket 200 may be reusable, requiring disposal of only the syringe 100 after use.

Figure 2A:
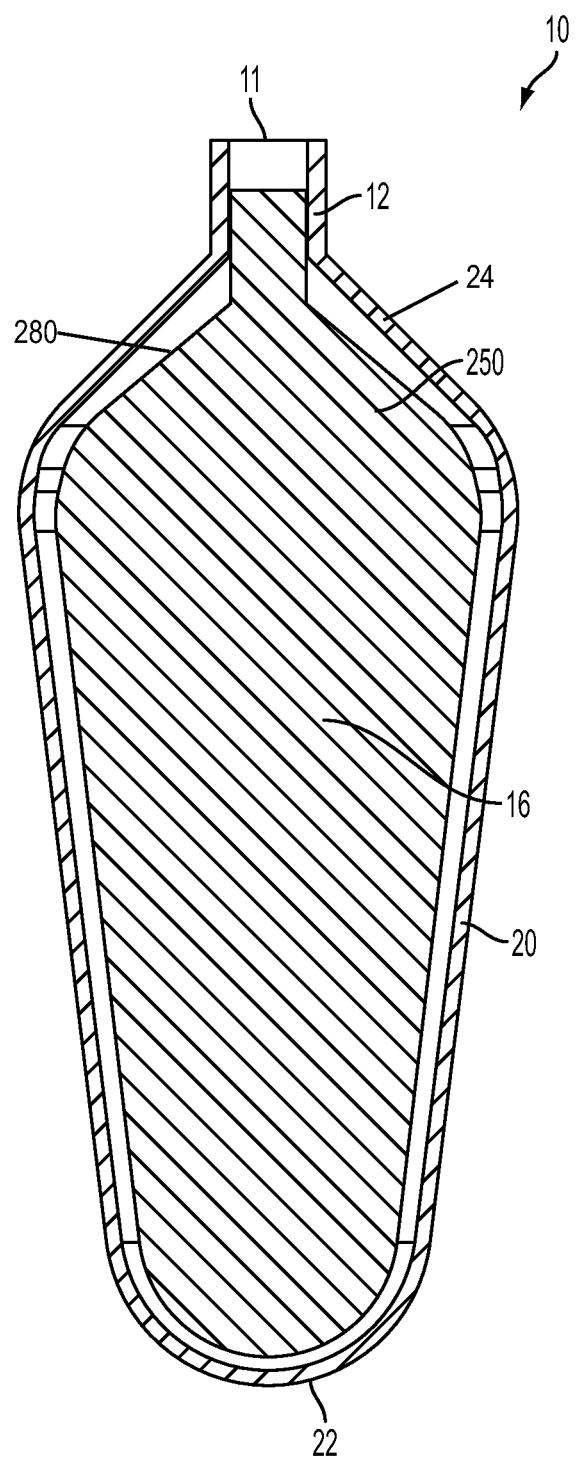
FIG. 2AB is a schematic drawing of an injection molded preform of FIG. 2A, after expansion by stretch blow molding, according to the principles of another embodiment.
Figure 2A:
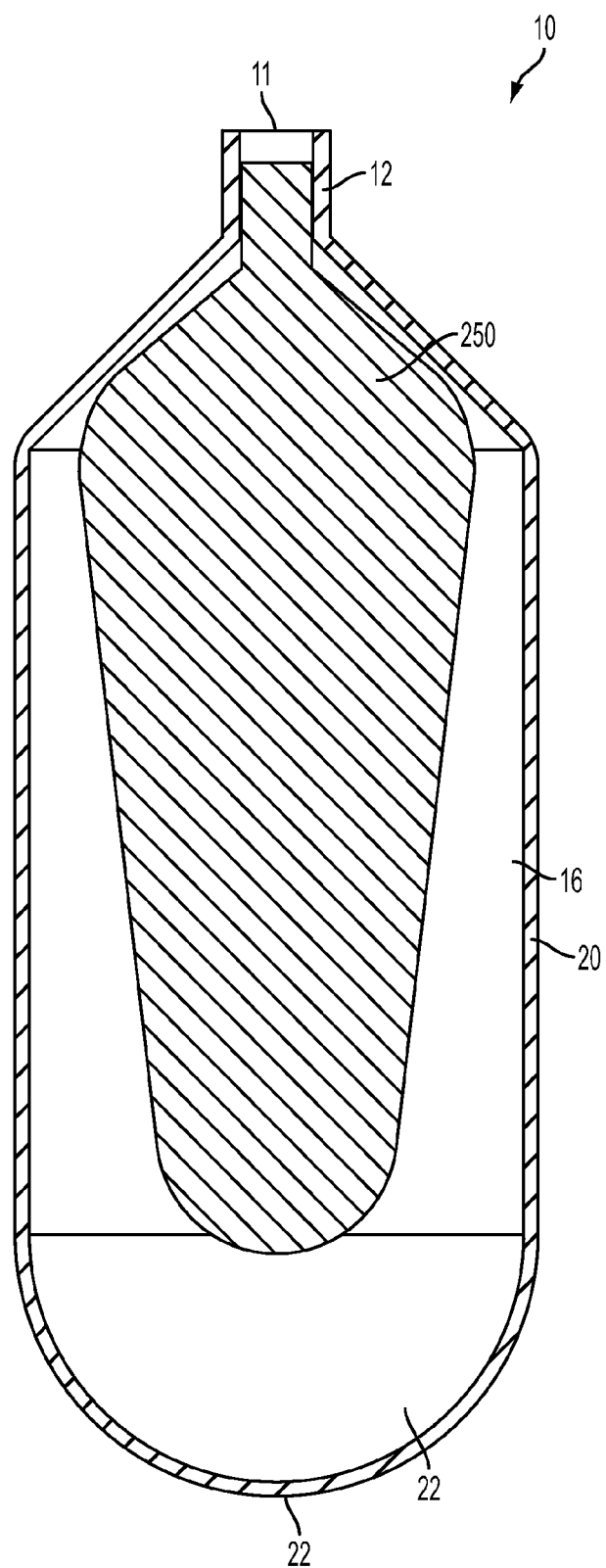
Figure 2B:
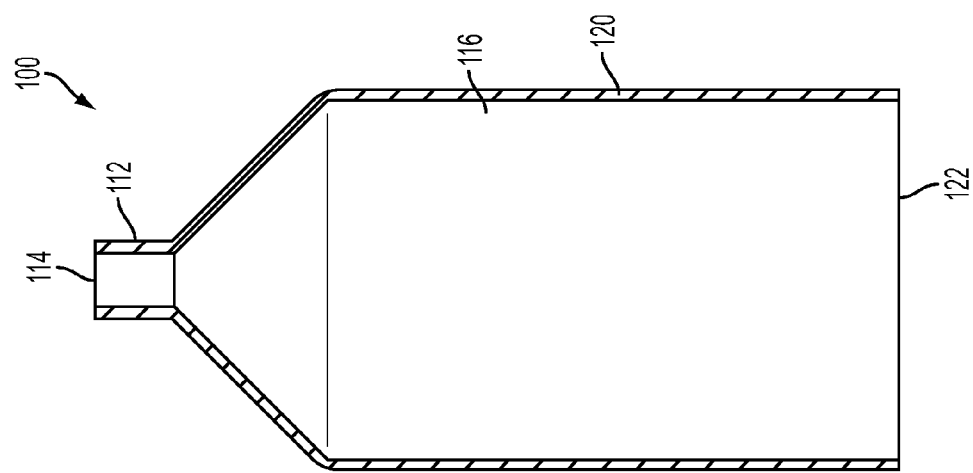
FIG. 2B is a schematic drawing of the injection molded syringe of FIG. 2AB, after removal of the stretch member and dome-shaped cap, according to the principles of another embodiment.
Figure 2B:
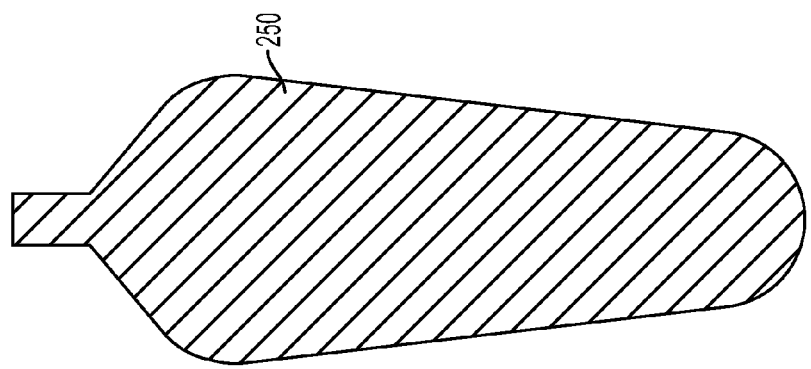
Figure 2C:
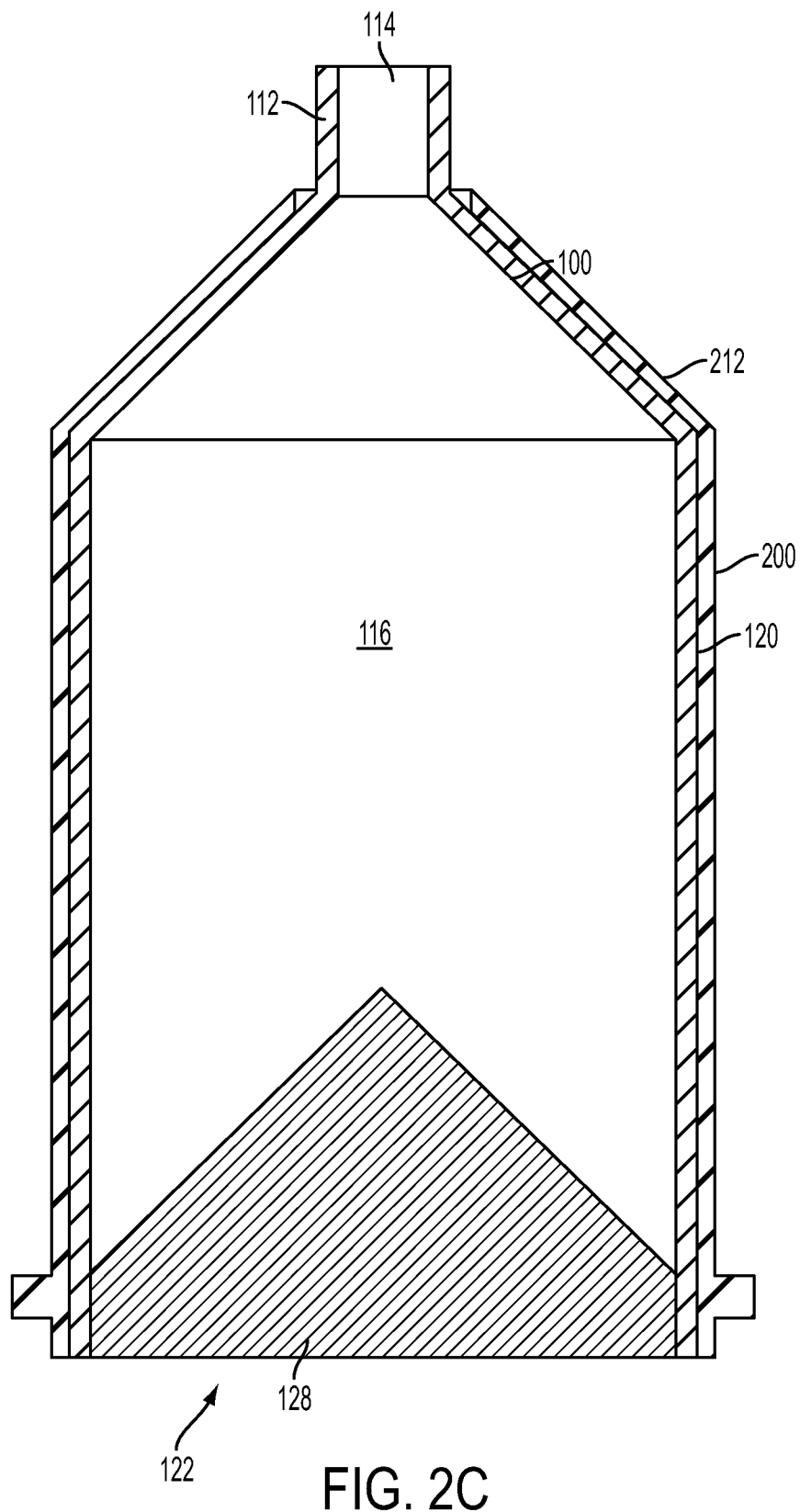
FIG. 2C is a schematic drawing of a syringe formed from the preform of FIG. 2A inserted in a pressure jacket.

With reference to FIGS. 2A-2C, a second embodiment of a preform 10 and a blow-molded syringe 100 is depicted. As with the previously described embodiment, the preform 10 includes a nozzle 12 with a first opening 11 for accessing an interior 16 of the preform 10. The preform 10 also includes an enclosed end 22. In FIG. 2A, the preform 10 is indicated in its initial state having a stretch member 250 that is injected molded into the interior 16 of preform 10 and is generally sized so that it can stretch the preform to the desired shape during stretch blow molding, including any undercut at the distal end of the preform 10. Stretch member 250 member has a diameter that is larger than the diameter of the first opening 11 and may have a substantially conical distal end 280 for forming the distal end of the preform 10 into a substantially conical shape during the stretch blow molding process. As illustrated in FIG. 2AB, the preform 10 is expanded by a stretch blow molding process and forms an expanded structure having a dome-shaped cap 24 at a proximal end 22 of the preform 10. The stretch member 250 may be formed from a material selected from the group consisting of a polymeric material having a glass transition temperature $T_g$ that is higher than the polymeric material of the preform 10, a composite material, and a metallic material. In certain embodiments, the stretch member 250 may further comprise a lumen and a plurality of ports for injecting air or other gas into interior 16 of preform 10 during the stretch blow molding process. The dome-shaped cap 24 is removed, such as by cutting the cap 24 from the wall 20, to form a syringe barrel 120 having a proximal opening 122. The stretch member 250 may then be removed from syringe 100 through the proximal opening 122 as shown in FIG. 2B.

Alternatively, the stretch member 250 may be a hollow container, for example formed from a plastic material having a high $T_g$. According to these embodiments, the preform 10 may be stretch blow molded around hollow stretch member 250 to form concentric hollow vessels. In some embodiments, cap 24 may be removed from preform 10 and a similar cap on stretch member 250 may be removed to form a structure that could be used as the body of concentric, co-axial syringes. In another embodiment, the end cap 24 may be retained and the resulting structure could be used concentric vessels for retaining two different fluids, one fluid in the hollow center of stretch member 250 and a second fluid in the hollow center of stretch blow molded preform 10. Caps may then be formed to enclose each vessel independently or a single cap may enclose both vessels. In one embodiment, the cap of the interior vessel from 250 can be removed to allow mixing of the two fluids. This may be advantageous in applications where a fluid mixture is required but must be mixed immediately prior to use or administration.

With reference to FIG. 2C, the finished syringe 100 is depicted inserted within a pressure jacket 200. The syringe 100 is loaded into the pressure jacket 200 and then inserted into the injector. According to these embodiments, the syringe 100 does not include notches for receiving bayonet locks for holding the distal end 126 of the syringe 100. Instead, the pressure jacket 200 includes a tapered distal portion 212 for supporting the syringe nozzle 112. The syringe 100 is held in the correct position by inserting the nozzle 112 into the tapered portion 212 of the pressure jacket 200.

Figure 3:
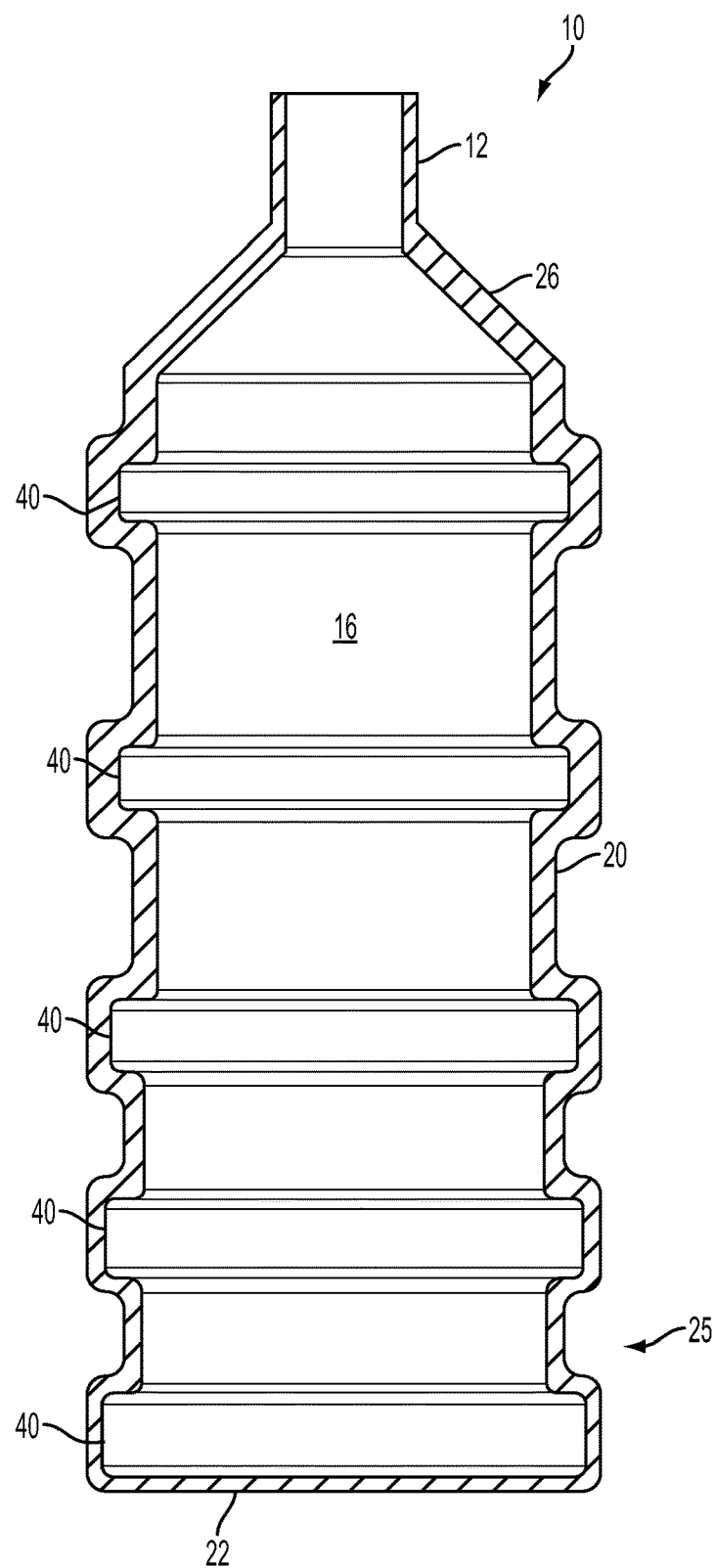
FIG. 3 is a schematic drawing of an injection molded preform, according to the principles of another embodiment.

With reference to FIG. 3, an embodiment of an injection molded preform 10 to be used for a stretch blow molding process is depicted. As in the above described embodiments, the preform 10 includes a nozzle 12, substantially cylindrical walls 20, and an enclosed end 22. A stretch rod may be inserted into an interior 16 of the preform 10 through the nozzle 12. Numerous ribs 40 are strategically spaced extending from the outer surface of the wall 20. The ribs 40 provide additional thermoplastic material that may be drawn into the walls 20 to form the barrel 120 of the finished syringe 100 following blowing molding and stretching. For example, the ribs 40 may be formed at a distal portion 26 of the preform 10 at a curved transition portion near the nozzle 12 such that the sidewall of the preform 10 is thicker in the area of the ribs 40 than the remaining portion of the preform 10. Such placement of the ribs 40 is advantageous in an embodiment where the distal end 26 of the syringe barrel 120 is formed at an angle, rather than an arc, to reduce the material stress at the transition point. In certain configurations, the ribs 40 become narrower and are spaced farther apart towards the distal end 26 of the preform 10 near the nozzle 12. The ribs 40 may provide additional material for stretching during the stretch blow molding process. Thus, since the proximal end portion 25 of the preform 10 farthest away from the nozzle 12 expands the least during stretching, less additional material is needed in that region of the preform 10. Following stretching and blow molding, the expanded preform 10 is a generally cylindrical structure having thin wall 20 of substantially uniform thickness. Strategic placement of the ribs 40 on the wall 20 provides for expansion of the preform 10 into a finished syringe 100 that has a substantially uniform wall 120 or a wall 120 with a portion that is selectively thicker than the remaining portion of the wall 120.

Figure 4A:
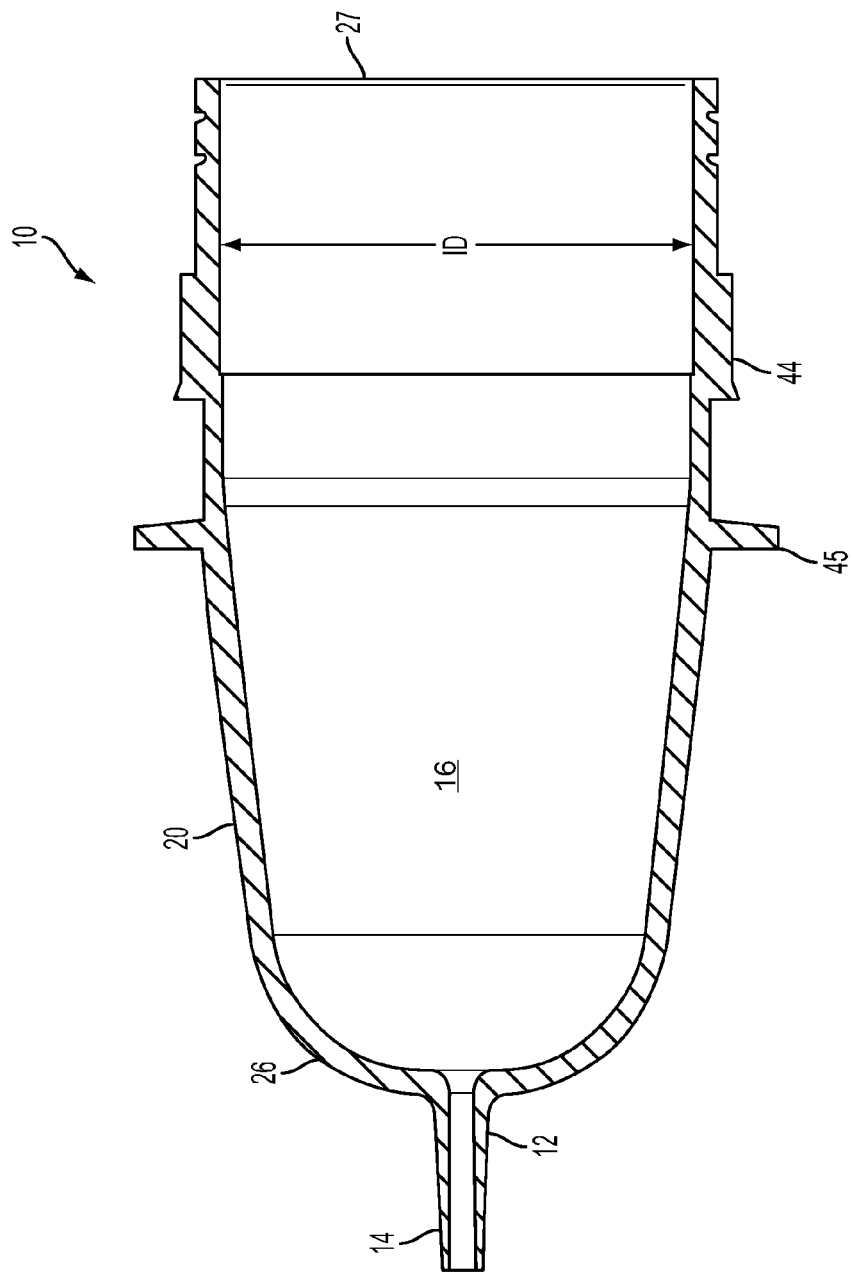
FIG. 4A is a schematic drawing of an injection molded preform, according to the principles of another embodiment.
Figure 4B:
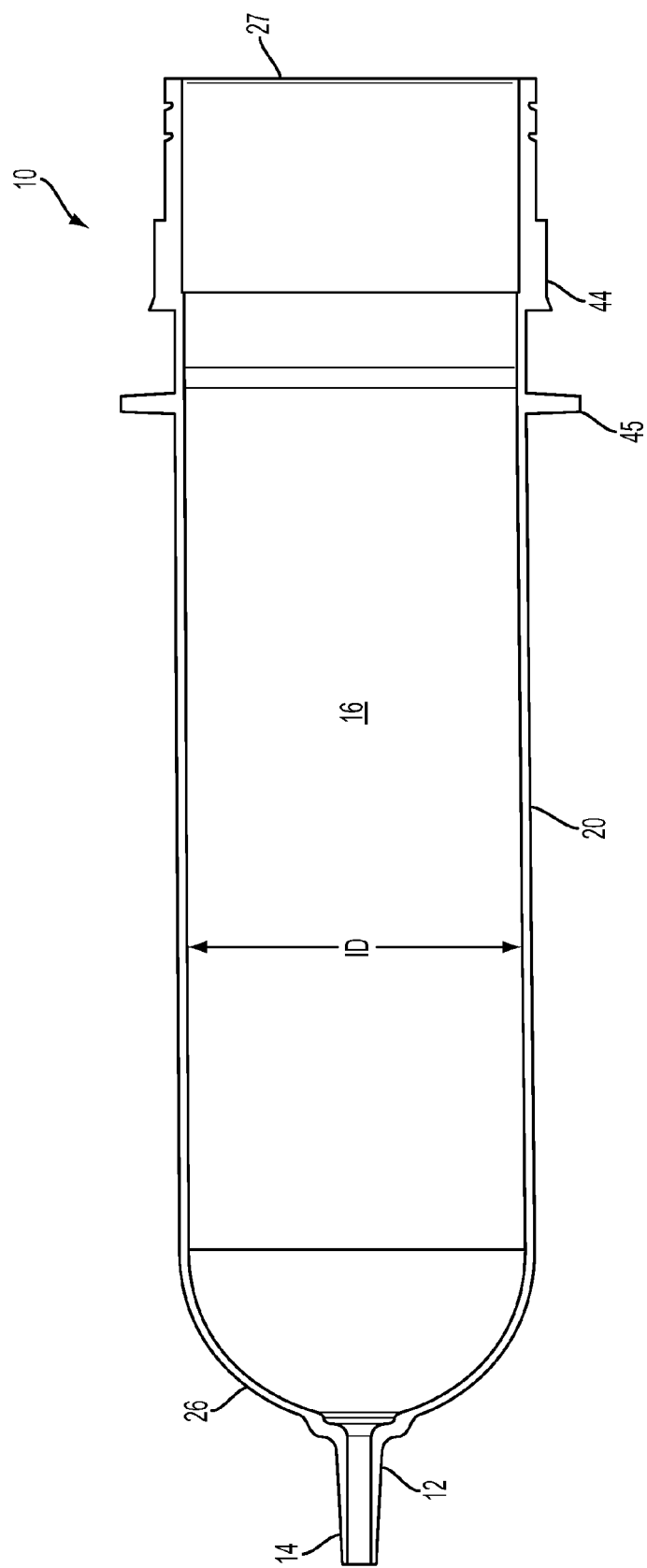
FIG. 4B is a schematic drawing of the preform of FIG. 4A, after expansion by stretch blow molding.
Figure 4C:
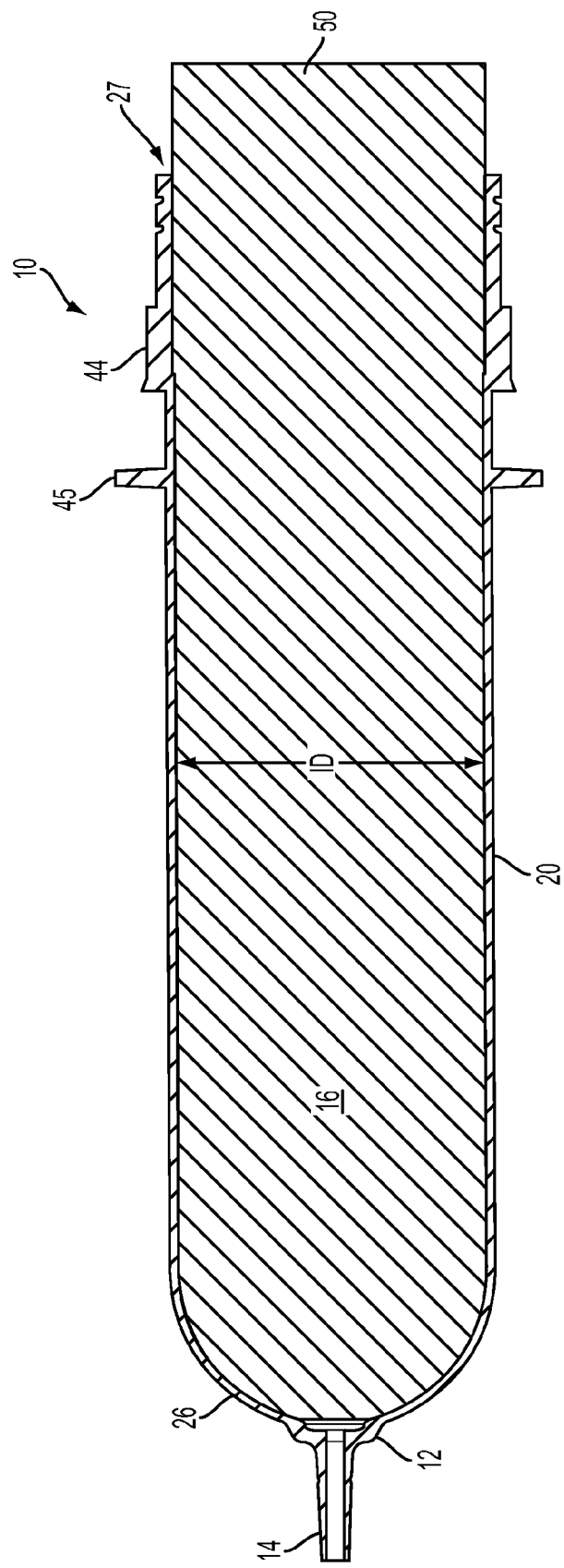
FIG. 4C is a schematic drawing of the preform of FIG. 4A with an inner core member inserted therein.

With reference to FIGS. 4A-4C, a further embodiment of a preform 10 and stretch blow-molded syringe 100 according to the principles of the present disclosure is depicted. As shown in FIG. 4A, the injection molded preform 10 has a second opening nozzle 12, a luer connector 14, a substantially cylindrical wall 20, and an expanded first opening 27 opposite the nozzle 12. The preform 10 may include various connection structures such as screw threads or at least one retaining member 44, positioned near the proximal opening 27 of the preform 10 for reversible engagement with a complementary locking member on a syringe port of a medical injector. These connection structures are used for attaching the syringe 100 to the injector. The proximal end of preform 10 may further include a drip flange 45 for preventing drips of medical fluid from nozzle 12 from entering into and generally fouling the interior workings and electronics of the medical injector. The proximal end of preform 10 may have an inner diameter ID that is substantially equal to the desired inner diameter of syringe 100.

The preform 10 is expanded by the stretch blow molding process described herein. However, in the present embodiment, the stretch rod is not inserted through the nozzle 12. Instead, access to the interior 16 of the preform 10 is provided through an opening 27. The stretch rod is inserted into the interior 16 of the preform 10 and presses against the end of the preform 10 near the nozzle 12, thereby causing the preform 10 to expand. The distal end of the stretch rod may contact and seal against the opening of the nozzle 12 to prevent air exposed to the interior 16 of the preform 10 from escaping during the blow molding process. Thus, the air causes the preform 10 to expand radially within the mold (not shown). As described herein, structural features of the preform 10 located near the opening 27 that receives the stretch rod are less likely to deform during stretching and blow molding than features located on other distal portions 26 of the preform 10. Therefore, the retaining members 44 and/or drip flange 45 located near the opening 27, including the inner diameter ID of the proximal end generally maintain their shape and size and, accordingly, may be injection molded with great specificity. In order to protect the deformation of the nozzle 12, the distal portion 26 of the preform 10 may be shielded from the heat that is applied to the preform 10 during the blow molding process. As such, the nozzle 12 may be able injection molded with tight tolerances or dimensional specificity. An expanded preform 10, produced by the blow molding process, is depicted in FIG. 4B.

With reference to FIG. 4C, in certain embodiments stretch blow molding may not allow for good control of the inner diameter ID of a container, since only the outer portion of the container contacts the mold. Accordingly, stretch blow molding may not always produce a fluid container having an inner diameter ID within a tight tolerance required for medical devices making it difficult to accurately determine volume of a blow molded container. Syringes for medical use generally must be manufactured within a tight tolerance to ensure that the correct amount of medical fluid is delivered to a patient. In view of these difficulties, certain embodiments of the blow molding process may include a reverse blow molding step so that the inner diameter ID of the syringe may be manufactured within a tight tolerance, appropriate for medical and diagnostic instruments.

More specifically, the preform 10 is initially stretch blow molded to an expanded state having an inner diameter slightly larger than the desired final inner diameter of the finished syringe. For example, the expanded preform 10 may be formed with an inner diameter 0.005 inches larger than desired. After the preform 10 is stretched and blow molded, a tight tolerance core 50 may be inserted into the interior 16 of the expanded preform 10, as shown in FIG. 4C. The preform 10 may then be heated and the outside of the preform 10 may be blown inward by application of pressure and/or vacuum around the tight tolerance core 50, thereby causing the preform 10 to shrink against the core 50. Alternatively, with certain thermoplastic materials, reheating the cooled stretch blow molded preform 10 with core 50 inserted therein, may result in shrinking of the thermoplastic of preform 10 around core 50 to produce the desired tight tolerances for the syringe inner diameter. As a result, the inner diameter ID of the preform 10 may be controlled within a tight tolerance offering greater control over syringe volume and shape compared with other stretch blow molding methods.

With reference to FIGS. 5A-5E, a further embodiment of a preform 10 and stretch blow molded syringe 100 is depicted. In this embodiment, the preform 10 is substantially identical to the preform 10 in the embodiment depicted in FIG. 4A and includes an opening 27 having retaining members 44 and optionally drip flange 45 extending therefrom, a cylindrical wall 20, and a bottom end having a nozzle 12 extending therefrom. As in the previously described embodiments, the preform 10 is stretch blow molded by heating to the $T_g$, inserting a stretch rod into the interior of the preform 10 and simultaneously blowing air into the interior 16 of the preform 10 causing radial expansion. The stretch rod may be configured to cover and seal the opening of the nozzle 12 to ensure that air does not escape during blow molding. The preform 10 may be blown to just below the approximate desired inner diameter ID and the stretch rod is removed. An expanding core member 52 capable of transitioning between a compressed state and an expanded state is then inserted in the blown preform 10 in the compressed state and the expandable core member 52 is expanded. The expandable core member 52 may be configured to press against the inner wall of preform wall 20 to increase the inner diameter ID of the expanded preform 10. Pressure from the expanding core member 52 molds the inner diameter ID of the preform 10 to a desired shape, size and inner diameter. The expandable core 52 thereby produces a preform 10 having an internal diameter ID within a tight tolerance, which may not be achievable by blow molding alone. After the syringe barrel is molded to the correct internal diameter ID, the expandable core 52 is contracted to the compressed state and removed from the preform 10.

Figure 5A:
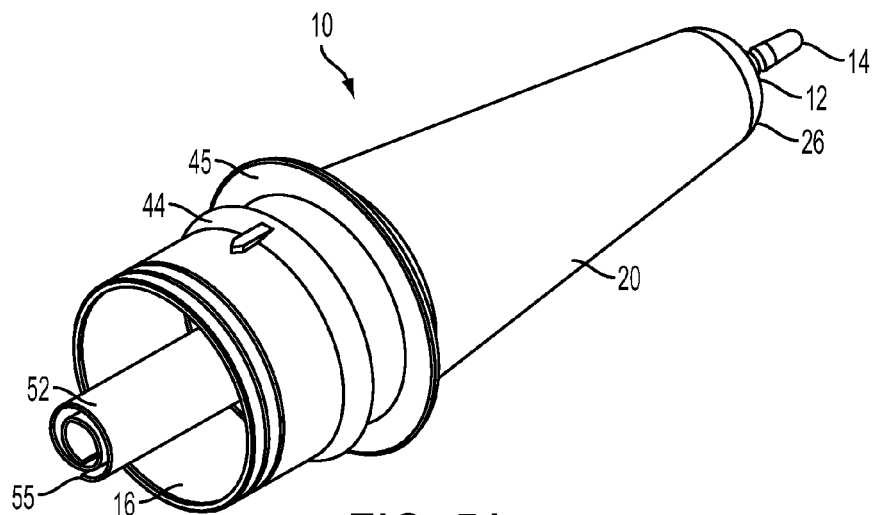
FIG. 5A is a schematic drawing of an injection molded preform, according to the principles of another embodiment.
Figure 5B:
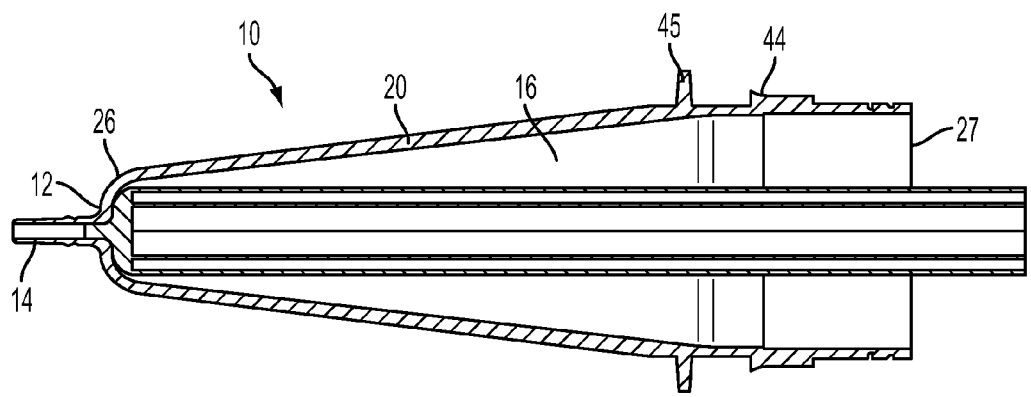
FIG. 5B is a perspective drawing of the preform of FIG. 5A.
Figure 5C:
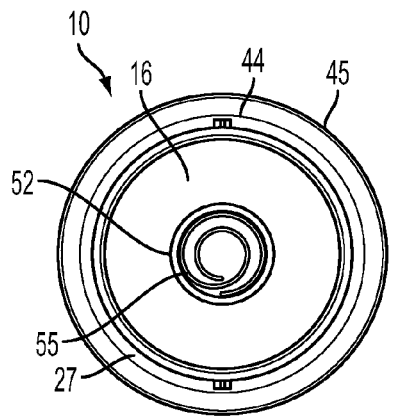
FIG. 5C is an endon view of the preform of FIG. 5A.
Figure 5D:
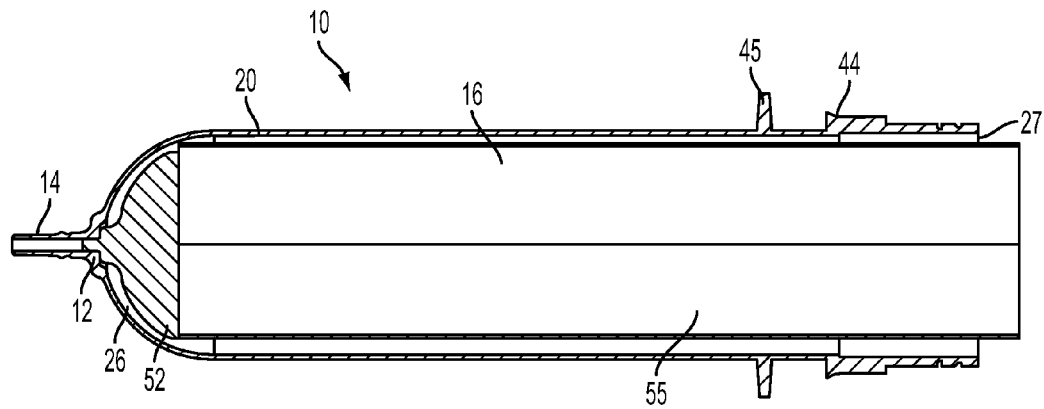
FIG. 5D is a cross section view of an expandable core, for use with the preform of FIG. 5A, in an expanded state.
Figure 5E:
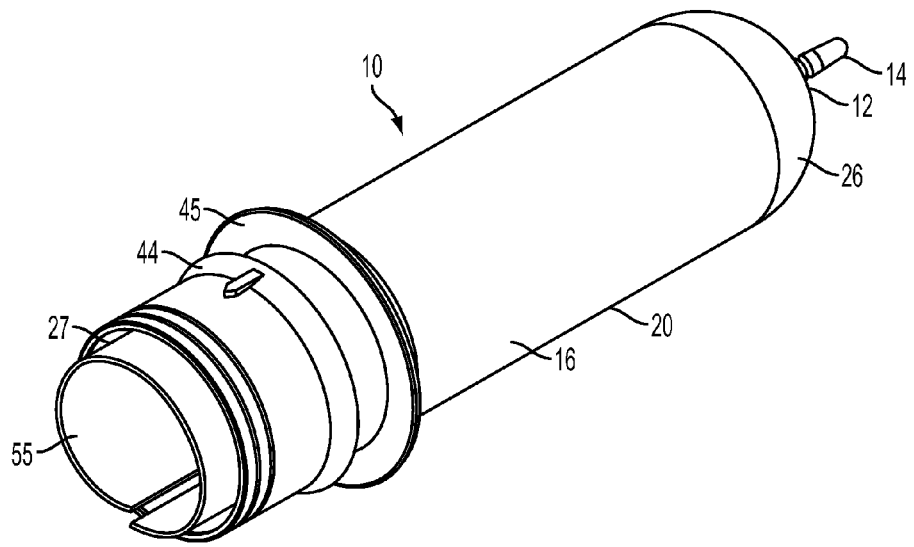
FIG. 5E is a perspective view of the expandable core of FIG. 5D, in an expanded state.
Figure 5F:
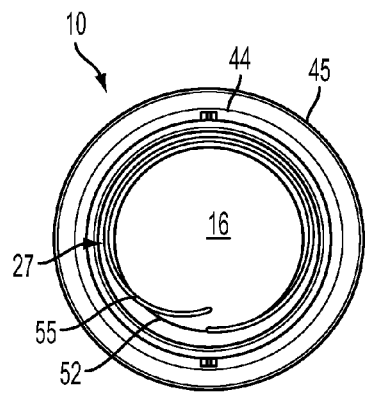
FIG. 5F is an end-on view of the expandable core of FIG. 5D, in an expanded state.

The expandable core 52 may have various structures capable of selectively transitioning from a compressed state to an expanded state. For example, the expandable core 52 may comprise a flexible sheet 55 wrapped or folded to form a coil around a central post. An exemplary core 52, having a coil 55 is depicted in FIG. 5A-F. The expandable core member 52 in the compressed state, with flexible sheet 55 tightly coiled around the central post is inserted into the interior 16 of preform 10 (see FIGS. 5A-C). The flexible sheet 55 may be released to an expanded state, as shown in FIG. 5D-F resulting in expansion of the interior 16 of preform 10 to a uniform inner diameter ID. The expandable core member 52 may then be contracted to the compressed state and removed from the preform 10. In other embodiments, the expandable core member 52 may comprise an inflatable structure, such as a balloon, which may be inflated to an expanded state, for example by pumping of a gas or fluid into an interior of the expandable core member 52.

Figure 6:
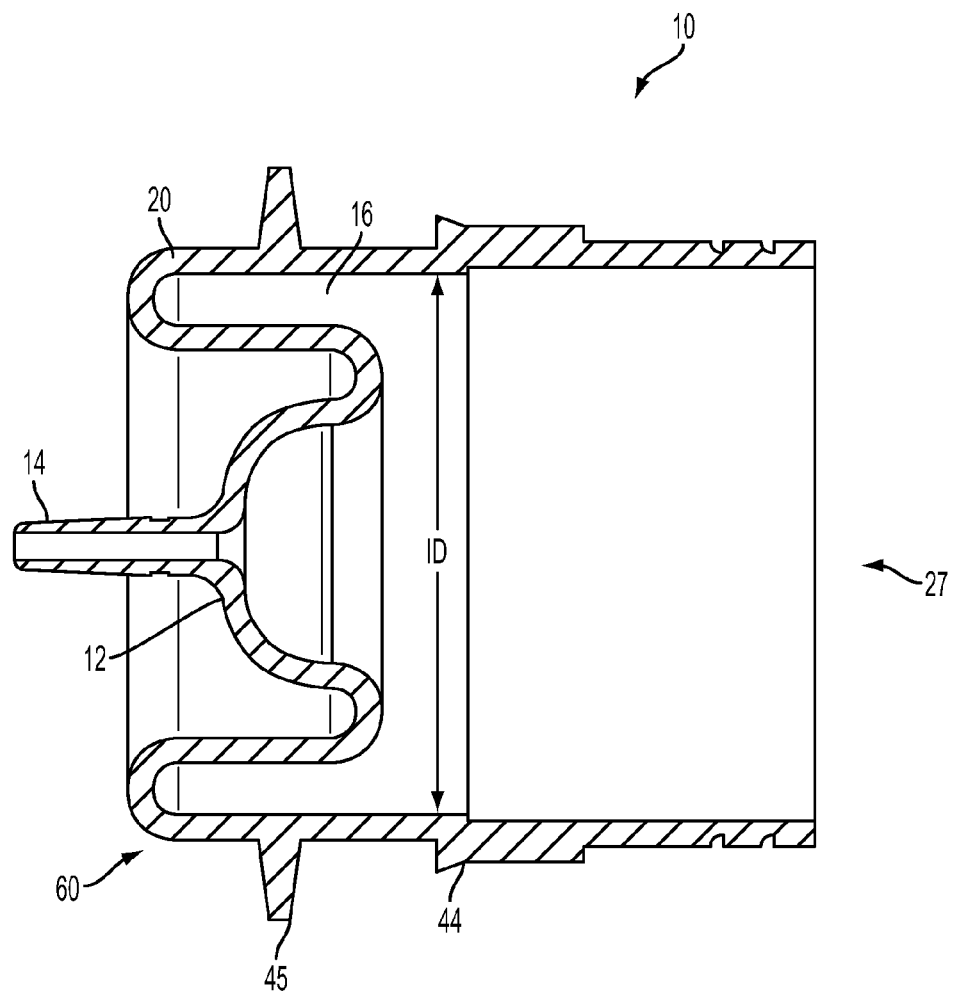
FIG. 6 is a schematic drawing of an injection molded preform, according to the principles of another embodiment.

With reference to FIG. 6, a further embodiment of a preform 10 for forming a syringe 100 by a stretch blow molding process is depicted. Unlike previous embodiments in which the preform 10 included substantially cylindrical walls 20, the preform 10 of FIG. 6 has one or more rolling diaphragm structures 60, and is generally a convolute form. As in previous embodiments, the preform 10 includes various retaining members 44 and/or drip flange 45 on the proximal end of the preform 10 near an opening 27. The preform 10 may also include a nozzle 12 opposite the expanded opening 27. The nozzle 12 may include an opening, which must be sealed by a stretch rod during blow molding. As a result of this structure, the preform 10 includes substantial amounts of material for axial and radial expansion. Specifically, regions on the inner diameter ID of the preform 10, such as within the diaphragm structure 60, may be provided with increased thickness. Thus, as the preform 10 and diaphragm structure 60 is expanded by the stretch rod and blown air, the thicker regions are distributed throughout the wall 20 of the preform 10, thereby providing a syringe barrel having a uniform wall thickness. It is noted that the preform 10 is formed by injection molding. Injection molding allows for formation of complex structures and shapes. Accordingly, the structural elements of the preform 10 can be formed with high precision, giving substantial control over the preform 10 shape and resulting stretching and expansion characteristics.

Figure 7A:
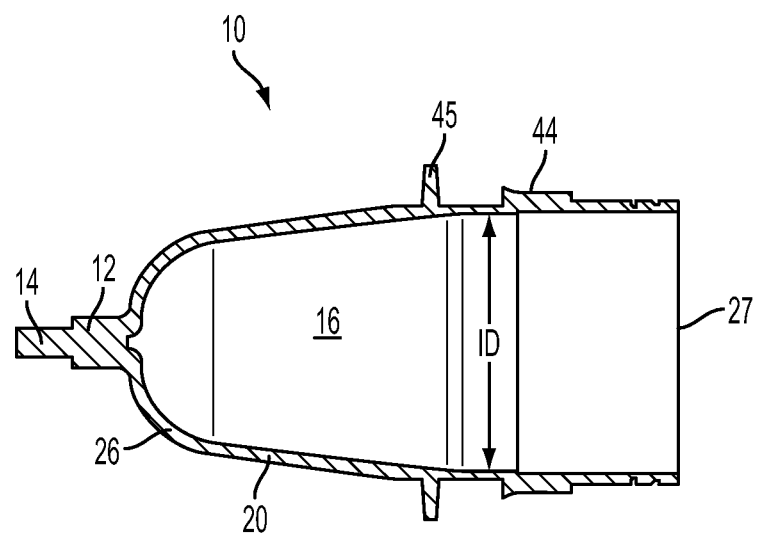
FIG. 7A is a schematic drawing of a preform, according to the principles of another embodiment.
Figure 7B:
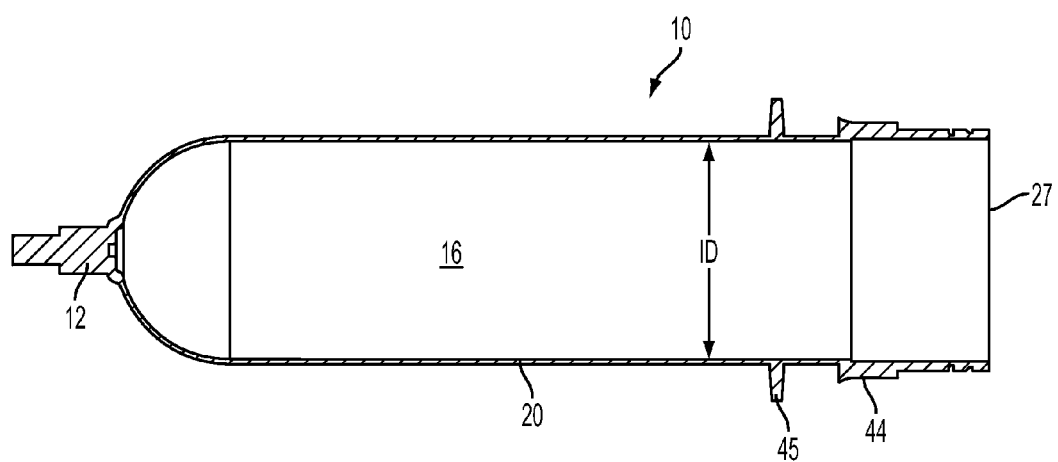
FIG. 7B is a schematic drawing of the preform of FIG. 7A in an expanded state.
Figure 7C:
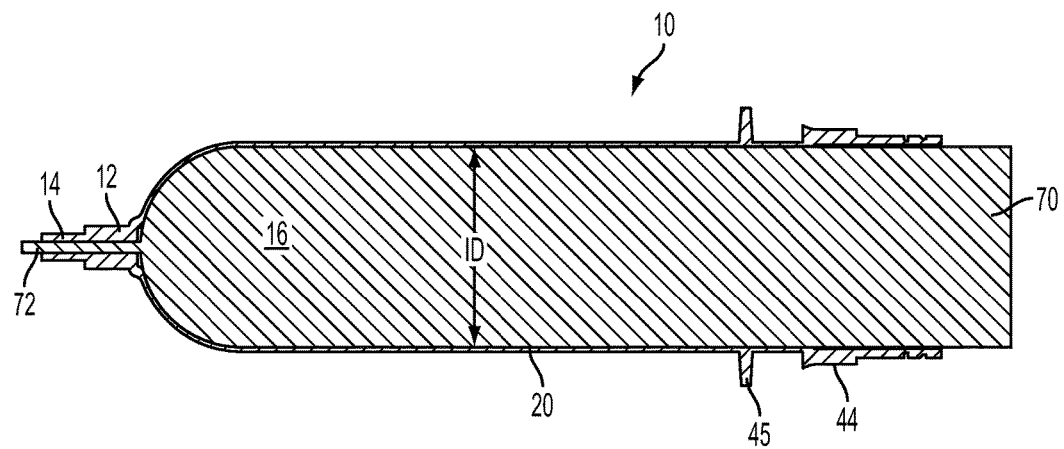
FIG. 7C is a schematic drawing of the preform of FIG. 7A, with an inner core inserted therein.

With reference to FIGS. 7A-7C, a further embodiment of a preform 10 and stretch blow-molded syringe 100 is illustrated. As in previously described embodiments, the preform 10 includes external retaining members 44 and/or drip flange 45 near an opening 27 of the preform 10 and a generally cylindrical wall 20 extending from the opening 27 toward the distal end 26 of the preform 10. According to these embodiments, nozzle 12 does not include a fluid passageway to luer connector 14. Thus, this embodiment provides a preform 10 having only a single opening, specifically opening 27. As in other embodiments, the preform 10 is expanded by the stretch rod and air blown into the interior 16 of the preform 10 (see FIG. 7B). After the preform 10 is expanded into an approximately desired shape (or slightly undersized or slightly oversized), a plug 70 for controlling the inner diameter ID of the expanded preform 10 is inserted in the preform interior 16 through opening 27. The plug 70 may have an outer diameter ID slightly greater than the inner diameter of preform 10 and thus may increase the inner diameter ID of the expanded preform 10 slightly, to form a syringe barrel within a tight tolerance for the inner wall diameter. Alternatively, if the expanded preform 10 is slightly oversized, the wall 20 of the preform 10 may be shrunk down around the plug 70, to produce the desired inner diameter ID by applied heat and vacuum or pressure to cause the preform 10 to tightly shrink over the outer diameter plug 70. In certain embodiments, the stretch rod may also serve as plug 70.

In certain embodiment, the plug 70 may further include a piercing tip 72 at the distal end of the plug 70. The piercing tip 72 is inserted into the nozzle 12 of the expanded preform 10 to form an opening therein to allow fluid connection between interior 16 and luer tip 14 upon removal of plug 70. The piercing tip 72 may be formed extending from the distal end of plug 70. In another embodiment, the piercing tip may be movable between an extended position and a retracted position. According to this embodiment, plug 70 may be inserted with the piercing tip 72 in the retracted position, then after application of heat and pressure or vacuum to produce the desired inner diameter, the nozzle 12 may be heated and the piercing tip moved to the extended position wherein the piercing tip 72 pierces nozzle 12. The piercing tip 72 may then be retracted and plug 70 removed. The opening formed by the piercing tip 72 becomes the opening of the nozzle 112 of the syringe 100. Medical solution is expelled from the finished syringe 100 through the opening of the nozzle 112 and luer connector tip 114.

According to other embodiments, a preform 10 having a structure similar to the preforms 10 described in reference to FIG. 4A is produced by injection molding. For example, the preform 10 may include a proximal opening 27, cylindrical walls 20, a nozzle 12, and luer tip 14. As in the previously described embodiments, the preform 10 is stretched and blow molded by insertion of a stretch rod and blowing air through the opening 27 of the preform 10. Once the preform 10 is expanded to the desired dimensions, a secondary core, such as a tight tolerance core 50 having an outer diameter with specific tight tolerances, is inserted into the interior 16 of the preform 10 (see FIG. 4C).

According to these embodiments, the expanded preform 10 is then reheated above its glass transition point, and vacuum pressure or positive pressure is applied to the interior or exterior, respectively, of the expanded preform 10. For example, vacuum may be applied through a plurality of ports on core 50 that are attached to a vacuum source. The applied heat and vacuum pressure or positive pressure causes the preform 10 to tightly shrink over the core 50 thereby conforming the inner diameter of preform 10 to the tight tolerances of the outer diameter of core 50. The combination of heat and vacuum forces ensures that a tight connection between the expanded preform 10 and core 50 is created, thereby ensuring that the inner diameter ID of the syringe 100 is controlled within a tight tolerance. A challenge with a syringe 100 produced by shrinking the preform 10 body tightly around the core 50 may include removing the core 50 from the preform 10. According to certain embodiments, the core 50 may be tapered, for example slightly tapered from the proximal to distal end, such that the distal end has a slightly smaller diameter than the distal end. Furthermore, the core 50 does not include undercuts or radial features that could potentially become stuck as the core 50 is removed from the expanded preform 10. It is recognized that a preform 10 having a tapered distal end may be easier to remove from the expanded preform 10 since contact between the core 50 and cylindrical walls 20 of the expanded preform 10 is reduced as the tapered core 50 is removed. In certain embodiments, any non-uniformities in syringe 100 resulting from the tapering of core 50 may be accounted for by compressibility of the syringe plunger 128. In other embodiments, the core 50 may be a composite structure with a thin outer sheath around a semi-flexible inner core. Removal of the core 50 may then be accomplished by removal of the inner core, for example, by sliding the inner core out of the preform 10, leaving the thin outer sheath in contact with the inner surface of the cylindrical walls 20 of preform 10. The outer sheath may then be removed. This embodiment may result in reduced deformation of the inner surface of the cylindrical walls 20 of preform 10 due to removal of core 50. The inner core may be made of a lubricious material or be coated with a lubricious material to reduce the coefficient of friction between the inner core and the outer sheath, allowing the inner core to be removed more readily.

The above described embodiments of syringes formed by stretch blow molding have thinner walls compared with conventional syringes, which are typically formed by injection molding. Tests indicate that the volume of the wall may be reduced by as much as 50% (0.079 inches vs. 0.039 inches) compared with syringes manufactured by injection molding. It is recognized that the thinner wall may modify the relationship between the wall and plunger, which is intended to form a liquid tight seal against the wall. Particularly, the thinner walled barrel formed by stretch blow molding is more flexible than thicker walls from injection molding processes. Since normal plungers for syringes form a tight seal by compressing against a stiff syringe barrel, such plungers may demonstrate unsatisfactory results when used with flexible syringe barrels.

Figure 8A:
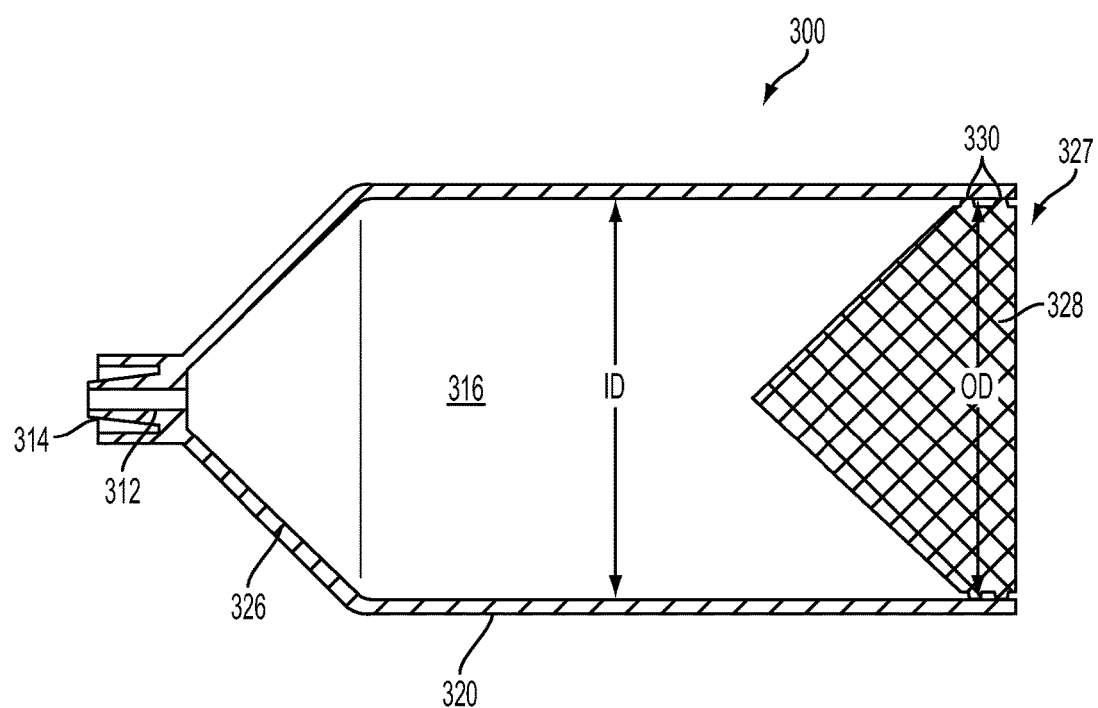
FIG. 8A is a schematic drawing of a syringe formed by stretch blow molding, according to the principles of another embodiment.
Figure 8B:
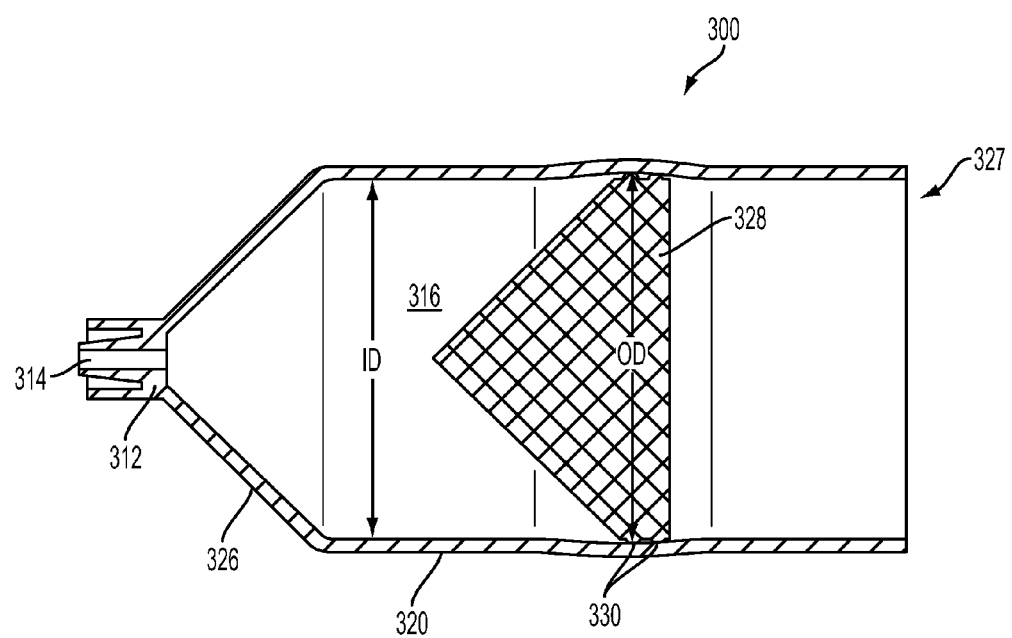
FIG. 8B is a schematic drawing of the syringe of FIG. 8A, with a plunger inserted therein.

Therefore, with reference to FIGS. 8A and 8B, a plunger 328 for a flexible syringe barrel 320, such as a syringe barrel 320 produced by a stretch blow molded process, is depicted. The plunger 328 is configured to be reversibly advanced through the syringe barrel 320 to expel fluid from the nozzle 312 located on the distal end 326 of a syringe 300. The plunger 328 has an outer diameter OD which is slightly larger than the inner diameter ID of the syringe barrel 320. Thus, when inserted into the syringe barrel 320, as shown for example, in FIG. 8A, the wall of the flexible barrel 320 deflects radially outward around the outer edge of plunger 328. The flexing creates a consistent sealing force to provide a leak proof seal between the flexible barrel 320 and the plunger 328. In certain embodiments, the difference between the OD of the plunger 328 and the ID of the syringe barrel 320 may be less than 1 mm, for example, in certain embodiments the difference between diameters may range from 0.1 mm to 1 mm.

The plunger 328 may include at least one radially extending ribs around the circumference, referred to herein as interference seals 330. The plunger 328 depicted in FIGS. 8A and 8B includes two such radially extending interference seals 330. Conventional syringe plungers generally include two or more compressible seals to ensure that a sufficient leak proof seal is created. Two or more seals may be required for conventional syringes due to the interaction between the relatively solid walls of the injection molded syringe barrel and the compressible seals on the plunger. However, since the presently described plunger 328 has a larger diameter than the syringe barrel 320, in certain embodiments the number of interference seals 330 could be reduced to one, without reducing the sealing ability of the plunger 328. In certain embodiments, reducing the number of interference seals 330 may reduce the force required to advance the plunger 328 through the syringe barrel 320. Due to the reduced friction of the interference seals 330 within the syringe barrel 330 compared to conventional, substantially rigid barrels, the number of interference seals 330 can be increased to meet the stringent sealing requirements in a pharmaceutical prefilled syringe.

A further benefit of using the plunger 328 and flexible walled syringe 300 is that the plunger 328 may be constructed from a stiffer material compared to standard syringe plungers. As described above, conventional pliable plungers are compressed against a stiff wall to form a seal. Therefore, the plunger must be sufficiently pliable and capable of deforming to form a tight seal. In contrast, in the presently described embodiment, flexible walled syringe barrel 320 flexes radially outward when contacted by the outer circumference of plunger 328, thereby forming a seal around the plunger 328. Thus, the plunger 328 is not required to be as pliable and deformable and, as a result, may be formed from a stiffer material than conventional plungers for use in stiff walled syringes. A stiffer plunger 328 reduces frictional forces between the plunger 328 and syringe barrel 320, while still maintaining a leak-proof seal. Accordingly, an injector using the syringe 300 and plunger 328 of the present disclosure would have lower power requirements and result in less strain on mechanical components of injector systems compared to presently used stiff walled syringes of a similar size. In addition, a stiffer plunger 328 may be manufactured as a single piece, rather than by a two-shot molding process, as is required by various conventional plungers, thus reducing overall costs of production.

Additionally, the presently described plunger 328 and blow-molded syringe barrel 320 having larger OD and smaller ID, respectively, may address other potential problems with blow-molded syringes. Specifically, in certain embodiments, it may be difficult to control the inner diameter ID of a blow-molded syringe barrel 320, since only the outer portion of the syringe barrel 320 is pressed against the mold during a stretch blow molded process. Therefore, there may be some inconsistency in the inner diameter ID of the syringe barrel 320. Using a plunger 328 having a slightly larger outer diameter OD than the inner diameter ID of the syringe barrel 320 effectively removes or addresses these potential inconsistency or non-uniformity, by ensuring that the plunger 328 sealably contacts the barrel 320 even if the inner diameter ID is slightly larger than expected. Therefore, a tight seal between the plunger 328 and the barrel 320 is formed even in the presence of some inconsistency or non-uniformity in the inner diameter ID of the barrel 320.

Figure 9A:
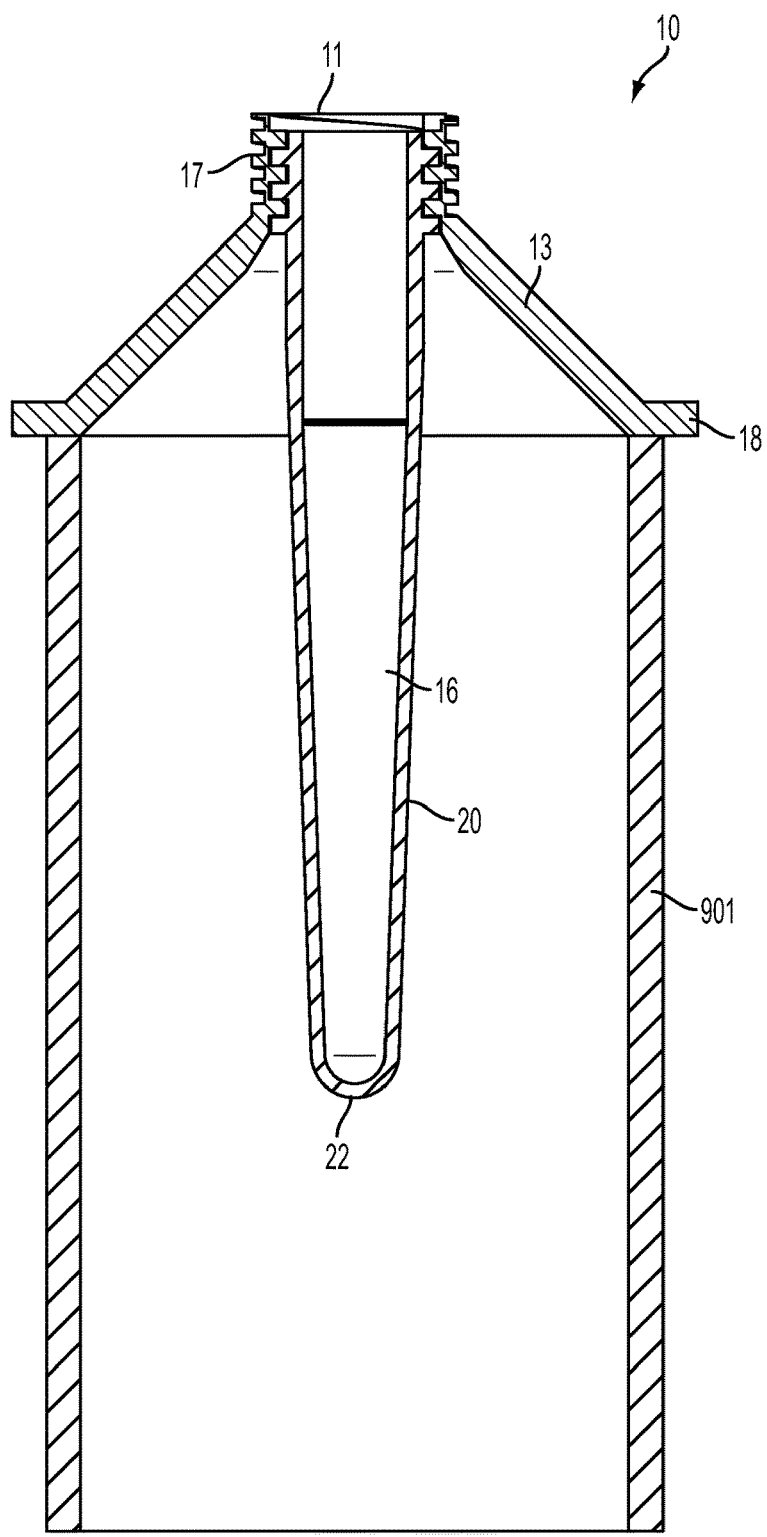
FIG. 9A is a schematic drawing of a preform in a mold, according to the principles of one embodiment.
Figure 9B:
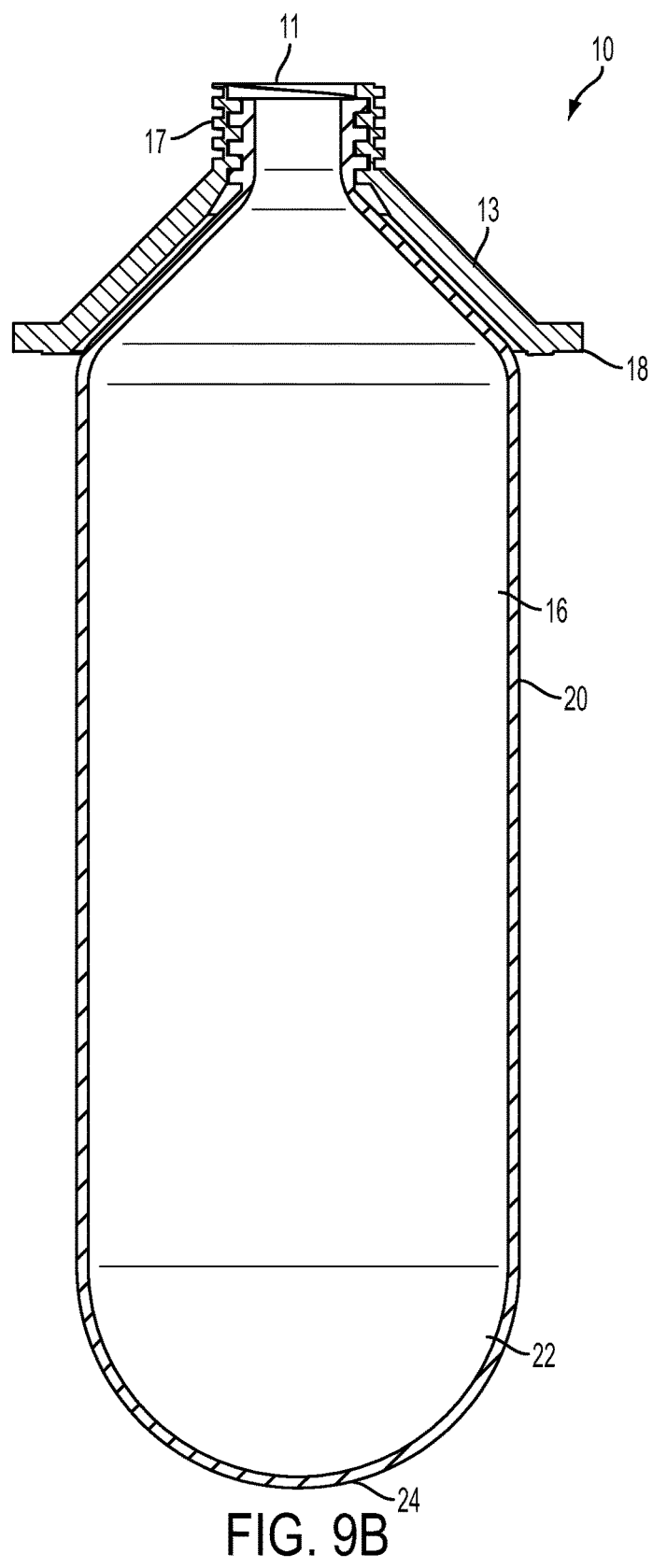
FIG. 9B is a schematic drawing of the preform of FIG. 9A in an expanded state.

Referring to an embodiment illustrated in FIGS. 9A-9G, a blow molded syringe preform 10 is described. As shown in FIG. 9A, a unitary preform 10 includes a conical shaped cap portion 13 having a distal opening 11 at the end of nozzle 12. Opening 11 includes threading 17 configured for threadably receiving a connector, wherein the threads may be on an outer wall (as shown) or an inner wall (not shown) of nozzle 12. Conical cap 13 also may include at least one bayonet lock members 18. Preform 10 further includes an expandable body having walls 20, interior space 16, and end portion 22. Conical cap 13 may be cooled during the stretch blow molding process to retain the structural features, such as threading 17, nozzle 12, and luer tip 14. Alternatively, conical cap 13 may be formed from a different material, such as a second polymeric material having a higher $T_g$ that the $T_g$ of the polymeric material of preform 10. As shown in FIG. 9A, preform 10 is inserted into mold 901 for the stretch blow molding process where a stretch rod may be inserted through opening 11. According to various embodiments, the diameter of opening 11, may be increased in size to accommodate larger diameter stretch rods. Preform 10 is submitted to a stretch blow molding process for form expanded preform 10 (shown in FIG. 9B). Expanded preform 10 further includes expanded wall 20 and end dome 24 at the proximal end 22 of preform 10.

Figure 9C:
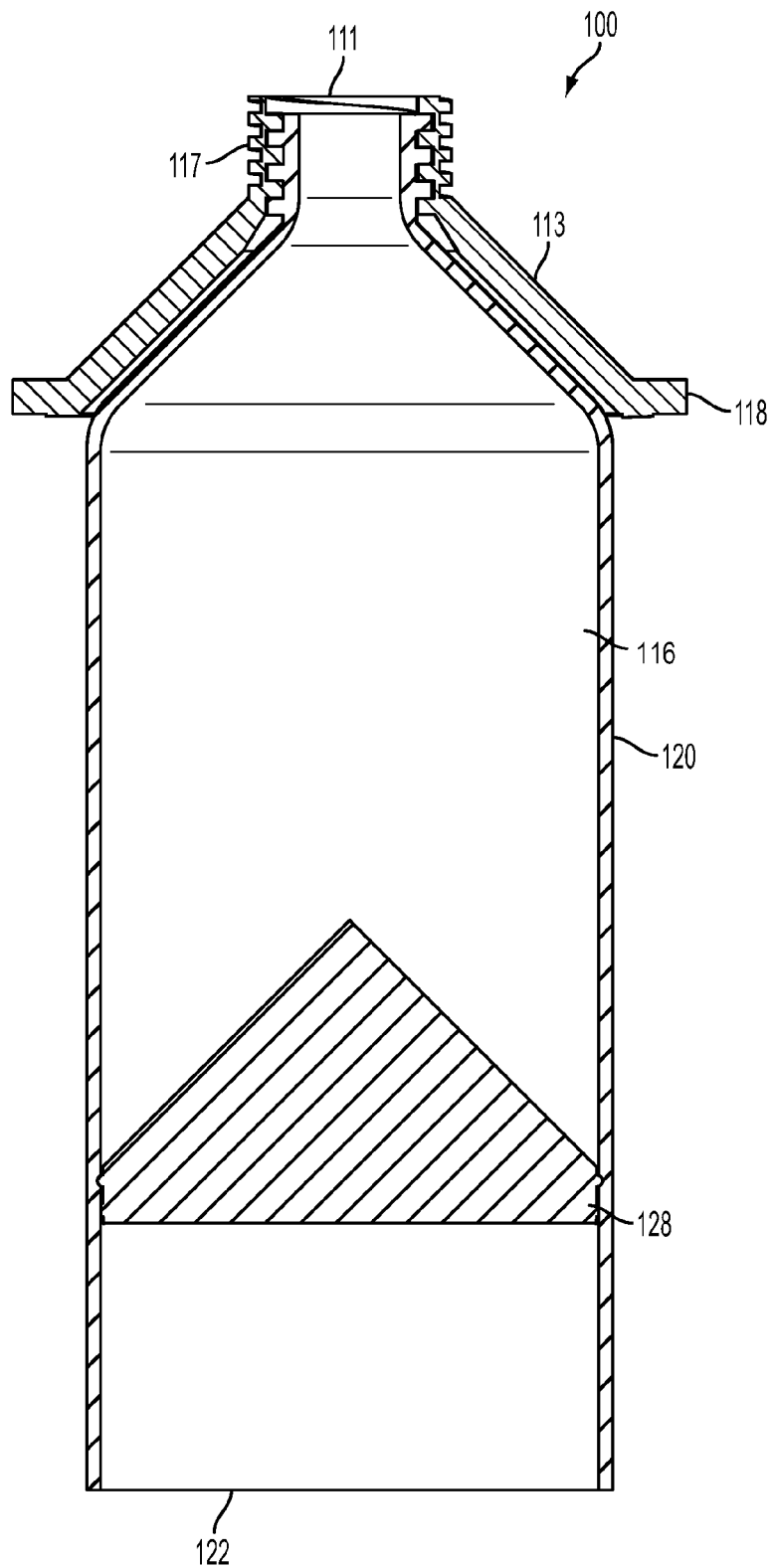
FIG. 9C is a schematic drawing of a syringe formed from the preform of FIG. 9A including a plunger.
Figure 9D:
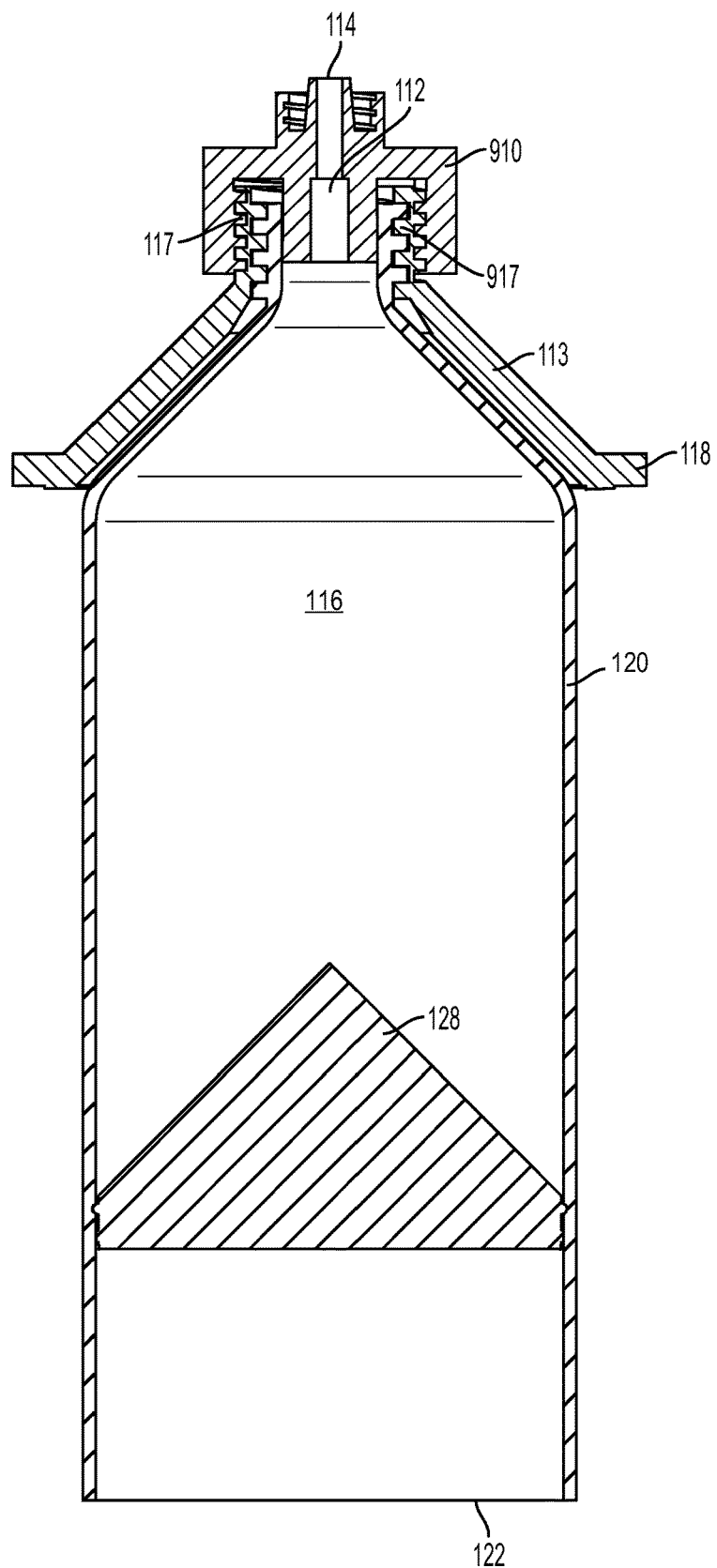
FIG. 9D is a schematic drawing of a syringe formed from the preform of FIG. 9A including a plunger and a luer connector.
Figure 9E:
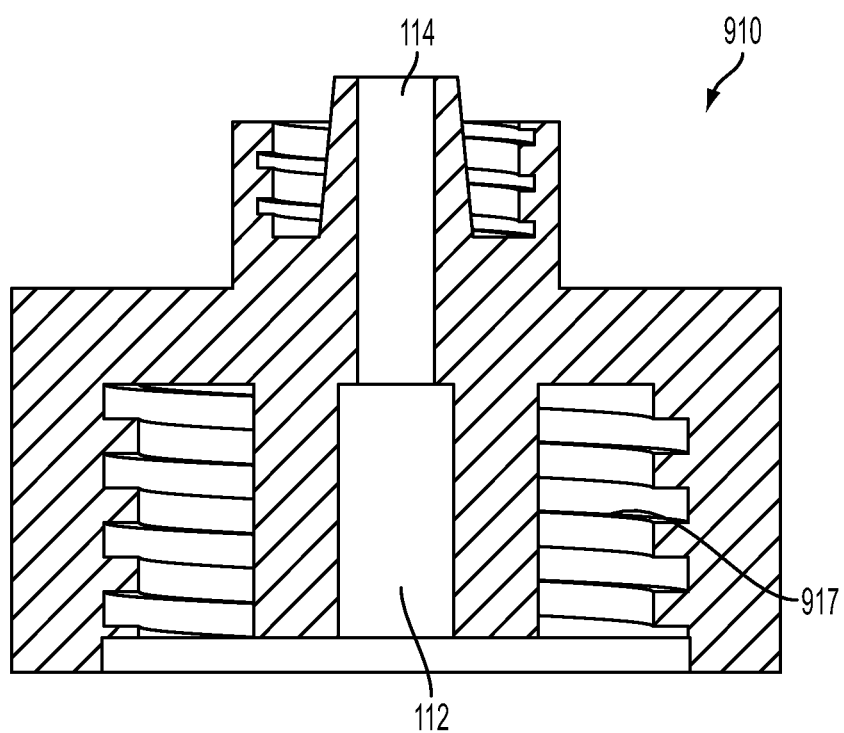
FIG. 9E is a schematic drawing of the luer connector of FIG. 9D.
Figure 9F:
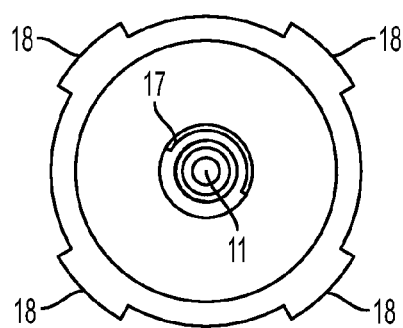
FIG. 9F is a top view of the preform of FIG. 9A.
Figure 9G:
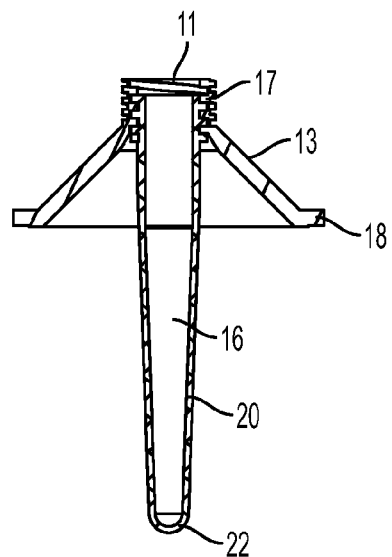
FIG. 9G is a side view of the preform of FIG. 9A without the mold.

Referring to FIG. 9C, end dome 24 is cut off the preform 10 and plunger 128 is inserted into opening 122 to form syringe 100 having distal opening 111 with threading 117. Referring to FIG. 9E, connector 910 is shown having a luer connection 114, and nozzle 112. Connector 910 has threads 917 that are complementary to and threadably received by threading 117 on syringe 100 to attach connector 910 to the distal end 113 of syringe 100, to provide fluid connection between the interior 116 of syringe 100 and luer tip 114 through nozzle 112 (see FIG. 9D). FIGS. 9F-G display top and side views, respectively, of preform 10. Syringe 100 may be received and locked into a pressure jacket, such as pressure jacket 200, shown in FIG. 1D, by interfacing of bayonet lock members 118, and corresponding notches or slots 210 on pressure jacket 200.

Figure 10:
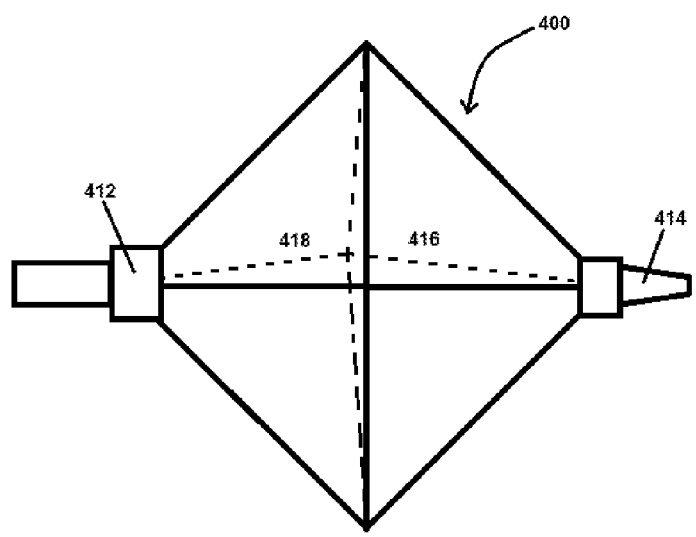
FIG. 10 is a schematic drawing of a syringe formed by blow molding, according to the principles of another embodiment.

Having described various embodiments of preforms and syringes formed by a stretch blow molding process, a further aspect of the disclosure directed to a blow molded syringe 400 will now be discussed. Therefore, with reference to FIG. 10, a further embodiment of a syringe 400 is depicted. The shape of the syringe 400 is chosen to be easily formed by blow molding, such as a polyhedral structure having a mirror plane perpendicular to the longitudinal axis from the proximal end of the syringe to the distal end of the syringe. Suitable structures include, for example, trigonal bipyrimidal polygons, octahedral polygons, pentagonal bipyrimidal polygons, hexagonal bipyrimidal polygons, and other bipyrimidal polygons having 7-x sides around the polygon, where x is an integer, up to and including syringe structures including two conic structures arranged on a mirror plane or two hemispheres or domes arranged on the mirror plane. When viewed from a top view, the syringe as represented in FIG. 10 is a substantially octahedral structure having a plunger attachment port 412 on one end and a luer nozzle 414 on an opposite end. The syringe 400 is constructed as a symmetrical structure, in which the front half 416 of the syringe 400 mirrors the back half 418 of the syringe 400. A reservoir (not shown) containing a fluid is contained in the front half 416, the back half 418, or a combination thereof of the syringe body. The back half 418 of the syringe 400 may be folded on the front half 416 of the body, thereby collapsing the syringe body and reservoir contained therein. Collapsing the fluid reservoir causes fluid to be expelled from the syringe 400 through the luer nozzle 414. In this configuration, the front half 416 is supported and fixed in place. The foldable back half 418 of the syringe 400 is rigid, yet flexible enough to fold over the front half 416.

In a further aspect of the disclosure, a method for testing a syringe barrel produced by stretch blow molding is disclosed. Comparing the blow-molded barrel to similar barrels produced by injection molding provides useful information concerning the performance of newly created blow-molded syringes. Specifically, it is suggested to consider starting with a small-sized prototype syringe. The performance of the prototype syringe may be compared to the performance of similarly sized syringes produced entirely from injection molding. This small scale comparison allows a user or technician to evaluate physical characteristics of syringes produced by stretch blow molding. Based on the evaluation of the smaller syringe, a user could determine whether a traditional sized syringe is able to be manufactured using a stretch blow molding method.

In a further aspect of the disclosure, a compacting system 500 for disposal of used syringes is disclosed. Presently, disposable syringes are collected in medical waste bags or containers. Medical facilities employ medical waste disposal companies to empty or remove the containers or bags. In larger medical facilities, the containers and medical waste bags must be emptied multiple times each day to avoid overfilling. Advantageously, syringes formed by stretch blow molding have a relatively low glass transition ($T_g$) temperature and may have thinner walls, making such syringes easily compactable. Furthermore, syringes formed by stretch blow molding are formed with smaller amounts of polymer material than comparable syringes formed by injection molding. Thus, substantial space may be saved by compacting such stretch blow-molded syringes.

The presently disclosed system 500 is configured to compact used syringes into a stackable cube 510 of plastic material. The cube could be sized to fit in a standard medical waste bag for safe handling. The system 500 generally resembles a standard kitchen compactor. However, unlike typical food compactors, the presently described system also includes a heating element for exposing the discarded syringes to a low temperature heat. Exposing the discarded syringes to a low heat of about 170° F. permits easier compacting of the used syringe barrel. The system 500 may further include elements for removing other components of the syringe (e.g. the syringe package tray, plunger/rubber cover, or the low pressure connector tube) from the syringe prior to heating. Although most syringes will be empty prior to insertion in the system 500, there may also be a mechanism for removing residual fluid from syringes, if necessary. However, if the entire compacted mass is identified as medical waste, then there would be no need to remove the medical fluid prior to compacting.

Figure 11:
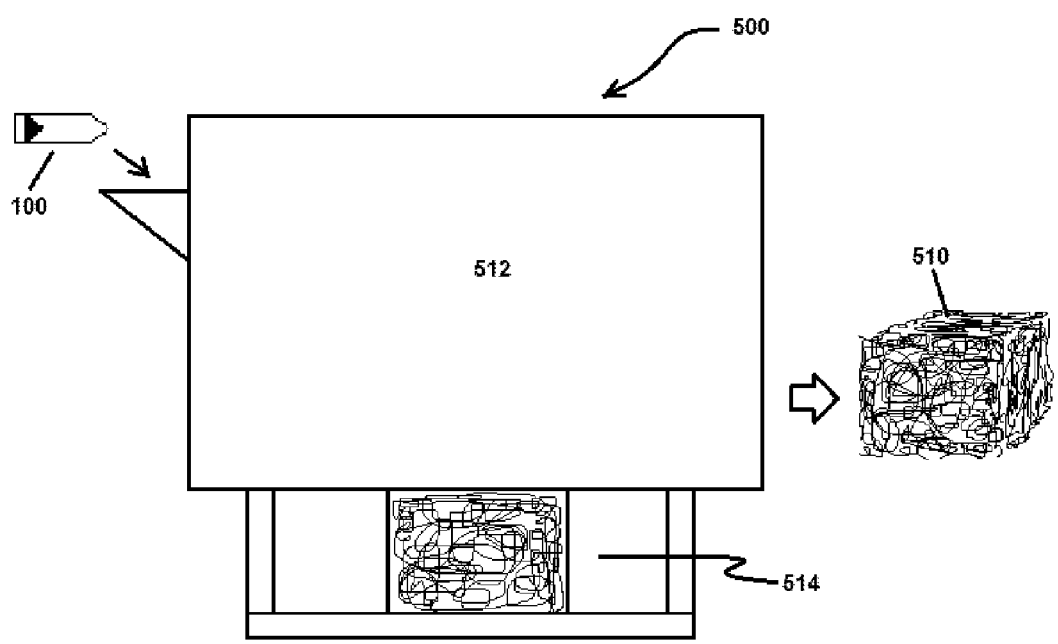
FIG. 11 is a schematic drawing of a system for compacting of disposable blow molded syringes, according to the principles of another embodiment.

With reference to FIG. 11, a schematic drawing of a syringe compacting system 500 is depicted. As shown in the schematic drawing, used blow-molded syringes 100 are placed into a heated chamber 512. The heated chamber 512 may also expose the used syringes to ultraviolet light for sterilization. After sterilization and heating, the discarded syringes 100 descend into a compactor 514 for compacting. The compactor 514 produces a generally cubical block 510 of compressed material. The block 510 may be recycled or may be thrown away as medical waste. The formed block 510 may be a variety of sizes depending on the needs of a particular medical facility. For example, the block 510 may be large enough to contain all disposable syringes 100 used at the facility during the day. Alternatively, blocks 510 of discarded disposables may be produced throughout the day using the compactor and stacked for easy storage until they can be disposed of. In either case, disposing of a compacted block 510 is more cost efficient and less labor intensive than disposing of discarded syringes 100 from medical waste containers multiple times throughout a day.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

We claim:

1. A preform for stretch blow molding a syringe, the preform comprising:
    a body having a distal end, an enclosed proximal end, and a circumferential wall therebetween and comprising a polymeric material suitable for stretch blow molding to form a syringe body; and
    a nozzle comprising a first opening at the distal end of the body for inserting a stretch member for stretching the preform during a stretch blow molding process,
    wherein the circumferential wall contains additional polymeric material arranged radially around the circumferential wall of the body toward the distal end,
    wherein the additional polymeric material forms a barrel of the syringe.

2. The preform according to claim 1, further comprising a second opening at a proximal end of the body, wherein the second opening is formed after the stretch blow molding process.

3. The preform according to claim 1, further comprising a cap for sealably enclosing the first opening, the cap having a substantially conical shape and a luer tip.

4. The preform according to claim 3, wherein the cap further comprises at least one bayonet lock member around an outer circumference of the cap for releasable locking engagement with at least one notch or slot on a pressure jacket configured for attachment to a medical injector.

5. The preform according to claim 1, wherein the body is formed having the stretch member in an interior of the body, wherein the diameter of the stretch member is larger than the diameter of the first opening at the distal end of the body and wherein the stretch member has a substantially conical end for forming the distal end of the preform into a substantially conical shape during the stretch blow molding process.

6. The preform according to claim 5, wherein the stretch member is formed from a material selected from the group consisting of a second polymeric material having a glass transition temperature higher than the polymeric material of the preform, a composite material, and a metal material.

7. The preform according to claim 5, wherein the stretch member further comprises a lumen and a plurality of ports for injecting a gas into the interior of the body during the stretch blow molding process.

8. The preform according to claim 5, wherein the stretch member is removed through a second opening at a proximal end of the body, wherein the second opening is formed after the stretch blow molding process.

9. The preform according to claim 5, wherein the substantially conical shape formed at the distal end of the preform is configured to fit into a pressure jacket comprising a substantially conical distal end.

10. The preform according to claim 1, further comprising a second opening at a proximal end for receiving a stretch member, wherein the stretch member seals the first opening during a stretch blow molding process through the second opening.

11. The preform according to claim 10, wherein the proximal end of the preform comprises at least one retaining member for reversible engagement with a complementary locking member on a syringe port of a medical injector.

12. The preform according to claim 10, wherein an inner diameter of a surface of an inner wall is molded by insertion of a core member through the second opening.

13. The preform according to claim 12, wherein the core member is an expandable core comprising a flexible sheet coiled around an inner member, wherein the flexible sheet may transition between a first compressed state and a second expanded state.

14. The preform according to claim 12, wherein the core member is an expandable core comprising an expandable balloon for receiving a fluid.

15. The preform according to claim 12, wherein the surface of the inner wall is molded around the core member by application of vacuum or pressure and heat to shrink the inner walls of the preform against the core member.

16. The preform according to claim 15, wherein the core member is tapered from a proximal end to a distal end.

* * * * *

UNITED STATES PATENT AND TRADEMARK OFFICE
CERTIFICATE OF CORRECTION

PATENT NO. : 10,328,208 B2
APPLICATION NO. : 15/032425
DATED : June 25, 2019
INVENTOR(S) : Rhinehart et al.

Page 1 of 1

It is certified that error appears in the above-identified patent and that said Letters Patent is hereby corrected as shown below:

In the Specification
In Column 5, Line 11, delete "endon" and insert -- end-on --, therefor.
In Column 11, Line 56, delete "wall 120 or a wall 120" and insert -- wall 20 or a wall 20 --, therefor.
In Column 11, Line 57, delete "wall 120." and insert -- wall 20. --, therefor.
In Column 13, Line 43, delete "FIG. 5A-F." and insert -- FIGS. 5A-F. --, therefor.
In Column 13, Line 48, delete "FIG. 5D-F" and insert -- FIGS. 5A-F --, therefor.
In Column 17, Lines 65-66, delete "bipyrimidal" and insert -- bipyramidal --, therefor.
In Column 17, Line 66, delete "bipyrimidal" and insert -- bipyramidal --, therefor.
In Column 17, Line 67, delete "bipyrimidal" and insert -- bipyramidal --, therefor.
In Columns 17 & 18, Lines 67 & 1, delete "bipyrimidal" and insert -- bipyramidal --, therefor.

Signed and Sealed this
Fifteenth Day of October, 2019

Andrei Iancu
*Director of the United States Patent and Trademark Office*